United States Patent
Kakita et al.

(10) Patent No.: US 8,633,380 B2
(45) Date of Patent: Jan. 21, 2014

(54) PHOTOELECTRIC CONVERSION ELEMENT COMPRISING BINUCLEAR RUTHENIUM COMPLEX DYE HAVING A SUBSTITUTED BIPYRIDYL GROUP, AND PHOTOCHEMICAL CELL

(75) Inventors: Kazuaki Kakita, Ichihara (JP); Takafumi Iwasa, Ichihara (JP); Yoshihisa Kakuta, Tokyo (JP); Masashi Shirai, Ube (JP); Toshio Furuya, Ube (JP); Shigeyoshi Nishino, Ube (JP); Hidetaka Shima, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 0 days.

(21) Appl. No.: 13/635,226

(22) PCT Filed: Mar. 15, 2011

(86) PCT No.: PCT/JP2011/056110
§ 371 (c)(1),
(2), (4) Date: Sep. 14, 2012

(87) PCT Pub. No.: WO2011/115137
PCT Pub. Date: Sep. 22, 2011

(65) Prior Publication Data
US 2013/0014824 A1    Jan. 17, 2013

(30) Foreign Application Priority Data

Mar. 16, 2010 (JP) .................. 2010-059487
Mar. 29, 2010 (JP) .................. 2010-074552
Mar. 29, 2010 (JP) .................. 2010-074553
Oct. 15, 2010 (JP) .................. 2010-232561
Nov. 30, 2010 (JP) .................. 2010-266254

(51) Int. Cl.
  H01G 9/20    (2006.01)
  H01L 51/48   (2006.01)
  H01L 51/46   (2006.01)

(52) U.S. Cl.
  USPC ........... 136/263; 136/252; 136/243; 136/244; 438/85; 546/10; 546/2; 257/E51.015

(58) Field of Classification Search
  USPC ......... 136/263, 252, 243, 244; 438/85; 546/2, 546/10; 257/E51.015
  See application file for complete search history.

(56) References Cited

U.S. PATENT DOCUMENTS 4,927,721 A    5/1990   Gratzel et al.
5,084,365 A    1/1992   Gratzel et al.
(Continued)

FOREIGN PATENT DOCUMENTS

JP    H01-220380    9/1989
JP    A-2003-261536    9/2003
(Continued)

OTHER PUBLICATIONS

International Preliminary Report on Patentability and Written Opinion mailed on Nov. 1, 2012 in International Application No. PCT/JP2011/056110.

(Continued)

*Primary Examiner* — Golam Mowla
(74) *Attorney, Agent, or Firm* — Knobbe Martens Olson & Bear LLP

(57) ABSTRACT

The present invention relates to a binuclear ruthenium complex dye having a higher absorption coefficient and capable of absorbing light of longer wavelength for realizing a photoelectric conversion element and a photochemical cell which may convert solar light into electricity over a wide wavelength range and exhibit high photoelectric conversion efficiency; and a binuclear ruthenium complex dye for realizing a photoelectric conversion element and a photochemical cell which may have high durability.

22 Claims, 2 Drawing Sheets

(56) References Cited

U.S. PATENT DOCUMENTS

| | | | |
|---|---|---|---|
| 6,084,176 A * | 7/2000 | Shiratsuchi et al. | 136/263 |
| 6,291,763 B1 * | 9/2001 | Nakamura | 136/256 |
| 6,335,481 B1 * | 1/2002 | Watanabe | 136/263 |
| 6,376,765 B1 * | 4/2002 | Wariishi et al. | 136/263 |
| 2003/0152827 A1 * | 8/2003 | Ikeda et al. | 429/111 |
| 2004/0074532 A1 * | 4/2004 | Ikeda et al. | 136/250 |
| 2004/0099306 A1 * | 5/2004 | Hara et al. | 136/263 |
| 2004/0187918 A1 * | 9/2004 | Ikeda et al. | 136/263 |
| 2006/0130249 A1 * | 6/2006 | Ikeda et al. | 8/550 |
| 2006/0237059 A1 | 10/2006 | Kurihara et al. | |
| 2007/0265443 A1 | 11/2007 | Wu et al. | |
| 2008/0015356 A1 | 1/2008 | Kakuta et al. | |
| 2011/0100467 A1 | 5/2011 | Kakita et al. | |

FOREIGN PATENT DOCUMENTS

| | | |
|---|---|---|
| JP | A-2004-359677 | 12/2004 |
| JP | A-2007-302879 | 11/2007 |
| JP | A-2009-080988 | 4/2009 |
| WO | WO 2006/038587 A1 | 4/2006 |
| WO | WO 2009/154275 A1 | 12/2009 |

OTHER PUBLICATIONS

Kuang et al., "High Molar Extinction Coefficient Heteroleptic Ruthenium Complexes for Thin Film Dye-Sensitized Solar Cells" J. Am. Chem. Soc., vol. 128, No. 12, pp. 4146-4154, Mar. 7, 2006.

* cited by examiner

PHOTOELECTRIC CONVERSION ELEMENT COMPRISING BINUCLEAR RUTHENIUM COMPLEX DYE HAVING A SUBSTITUTED BIPYRIDYL GROUP, AND PHOTOCHEMICAL CELL

This application is the U.S. National Phase under 35 U.S.C. §371 of International Application No. PCT/JP2011/056110, filed Mar. 15, 2011, designating the U.S., and published in Japanese as WO2011/115137 on Sep. 22, 2011, which claims priority to Japanese Patent Application No. 2010-059487, filed Mar. 16, 2010; Japanese Patent Application No. 2010-074552, filed Mar. 29, 2010; Japanese Patent Application No. 2010-074553, filed Mar. 29, 2010; Japanese Patent Application No. 2010-232561, filed Oct. 15, 2010; and Japanese Patent Application No. 2010-266254, filed Nov. 30, 2010, the entire contents of which are incorporated herein by reference.

TECHNICAL FIELD

The present invention relates to a photoelectric conversion element comprising a binuclear ruthenium complex dye having a substituted bipyridyl group, and a photochemical cell comprising the photoelectric conversion element.

BACKGROUND ART

A solar battery is greatly expected to serve as a clean renewable energy source, and researches have been conducted for practical application of monocrystalline-silicon, polycrystalline-silicon or amorphous-silicon-based batteries and solar batteries comprising, for example, cadmium telluride or indium copper selenide. For the spread of solar battery as a household power source, however, any of these batteries faces many problems to be overcome, including a higher production cost, difficulty in ensuring raw materials, difficulty in recycling, and difficulty in realizing a larger area. Accordingly, there have been proposed solar batteries comprising an organic material in an attempt to achieve a larger area and a lower cost. However, any of these batteries has a conversion efficiency of about 1%, which falls very short of practical use.

Under such circumstances, Graetzel et al. disclosed a photoelectric conversion element and a solar battery comprising semiconductor particles sensitized by a dye, as well as materials and production technique needed to produce this solar battery, in 1991 (see, for example, Non-patent document 1 and Patent document 1). This battery is a wet solar battery comprising a porous titania thin film sensitized by a ruthenium dye as a working electrode. This solar battery has the advantages that the photoelectric conversion element can be provided at a low cost because inexpensive materials can be used without highly purification, and that the solar battery can convert solar light into electricity over a wide visible light wavelength range because the dye used in the solar battery has a broad absorption band. However, the conversion efficiency must be further improved for practical use. Thus, there is a need for development of a dye which has a higher absorption coefficient and absorb light of longer wavelength.

Patent document 2 discloses a mononuclear metal complex containing a dipyridyl ligand, which is a metal complex dye useful for a photoelectric conversion element. In addition, Non-patent document 2 discloses a polynuclear β-diketonate complex dye.

Meanwhile, Patent document 3 discloses a polynuclear complex containing a plurality of metals and a plurality of ligands wherein a bridging ligand (BL) coordinating to the plurality of metals has both a coordination structure with a conjugated heterocyclic ring and a coordination structure without a conjugated heterocyclic ring, which is regarded as a novel polynuclear complex having the excellent photoelectric conversion function of emitting electrons while receiving energy from active ray such as light.

In addition, Patent document 4 discloses a binuclear metal complex having a coordination structure with a conjugated heterocyclic ring, which is a metal complex dye for realizing a photoelectric conversion element having higher photoelectric conversion efficiency.

CITATION LIST

Patent Document

Patent document 1: JP-A-1989-220380
Patent document 2: JP-A-2003-261536
Patent document 3: JP-A-2004-359677
Patent document 4: WO 2006/038587 A1

Non-Patent Document

Non-patent document Nature, Vol. 353, p. 737, 1991
Non-patent document 2: "Current Technology in Dye-sensitized Solar Battery" (CMC Co., LTD., published on May 25, 2001, p. 117)

SUMMARY OF THE INVENTION

Problems to be Solved by the Invention

An objective of the present invention is to provide a metal complex dye having a higher absorption coefficient and capable of absorbing light of longer wavelength for realizing a photoelectric conversion element and a photochemical cell which may convert solar light into electricity over a wide wavelength range, and exhibit high photoelectric conversion efficiency. Another objective of the present invention is to provide a metal complex dye for realizing a photoelectric conversion element and a photochemical cell which may have high durability.

Means for Solving the Problems

The present invention relates to the following items.

<1> A binuclear ruthenium complex dye represented by the formula (1):

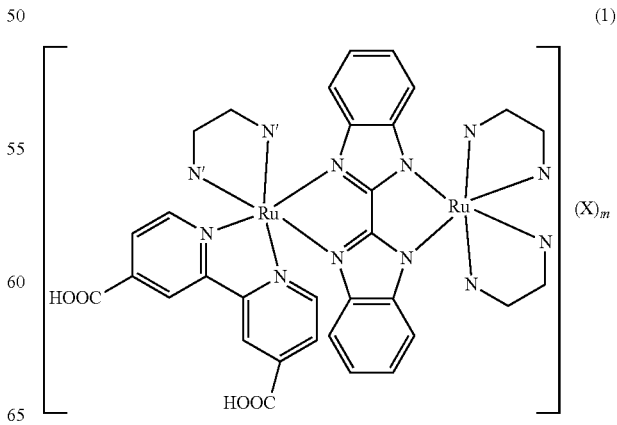

(1)

wherein
two

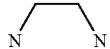

and

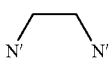

may be the same as, or different from each other, and each independently represents a group represented by the formula (2-1);

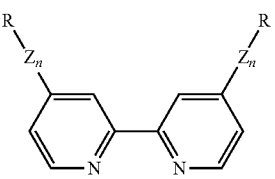

wherein
Z represents a 5-membered heteroarylene,
n represents a number of Z, which is an integer of from 0 to 4, and
R represents hydrogen, a linear or branched alkyl group having 1 to 18 carbon atoms, or carboxyl group,
with the proviso that two R may be the same as, or different from each other, and a plurality of Z may be the same as, or different from each other; or a group represented by the formula (2-2);

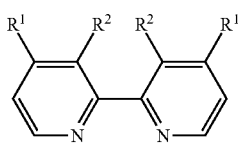

wherein
$R^1$ and $R^2$ each independently represents hydrogen, or a linear or branched alkyl group having 1 to 30 carbon atoms, or $R^1$ and $R^2$ present on the same pyridine ring or two $R^2$ may be joined together to form a ring,
with the proviso that two $R^1$ may be the same as, or different from each other, and two $R^2$ may be the same as, or different from each other; or a group represented by the formula (2-3):

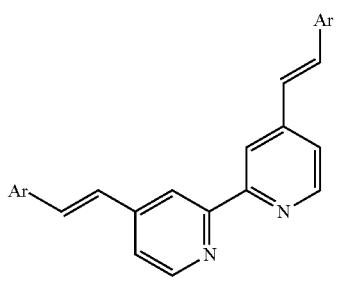

wherein
Ar represents an aryl group which may have a substituent, with the proviso that two Ar may be the same as, or different from each other; and
X represents a counter ion; and
m represents a number of the counter ions needed to neutralize a charge of the complex;
with the proviso that
at least one of two

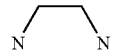

and

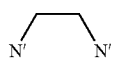

represents a group represented by the formula (2-1) in which n is an integer of from 1 to 4, or a group represented by the formula (2-3); or

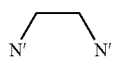

represents a group represented by the formula (2-2); and proton(s) (H+) of one or more carboxyl groups (—COOH) may dissociate.

<2> A photoelectric conversion element comprising a binuclear ruthenium complex dye as described in <1>; and a semiconductor particle.

<3> A photoelectric conversion element as described in <2>, wherein the semiconductor particle is at least one selected from the group consisting of titanium oxide, zinc oxide and tin oxide.

<4> A photochemical cell comprising a photoelectric conversion element as described in <2>.

<5> A photochemical cell comprising a photoelectric conversion element as described in <2> as an electrode, a counter electrode, and an electrolyte layer between them.

<6> A process for producing a photoelectric conversion element, comprising a step of:
immersing a semiconductor particle in a solution containing a binuclear ruthenium complex dye as described in <1>.

<7> A process for producing a photoelectric conversion element, comprising steps of:

forming a semiconductor layer comprising a semiconductor particle on a conductive support; and immersing the semiconductor layer in a solution containing a binuclear ruthenium complex dye as described in <1>.

Effect of the Invention

According to the present invention, there may be provided a metal complex dye having a higher absorption coefficient and capable of absorbing light of longer wavelength. There may be provided a photoelectric conversion element and a photochemical cell, which may convert solar light into electricity over a wide wavelength range, and exhibit high photoelectric conversion efficiency, by means of the metal complex dye.

According to the present invention, there may be also provided a metal complex dye for realizing a photoelectric conversion element and a photochemical cell which may have high durability.

DESCRIPTION OF EMBODIMENTS

Figure 1:
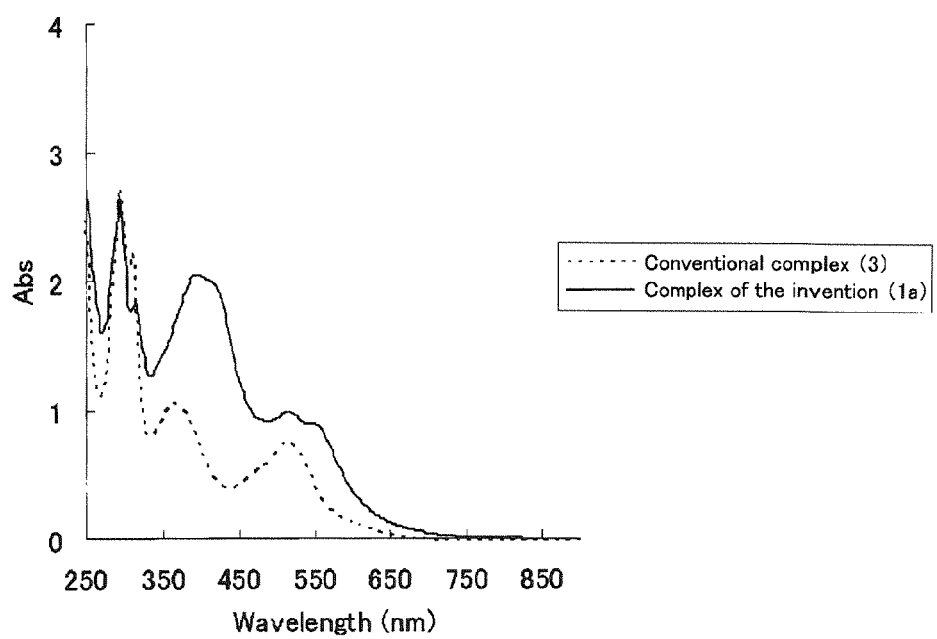
FIG. 1 is ultraviolet-visible absorption spectra of the binuclear ruthenium complex (1a) and the conventional binuclear ruthenium complex (3).

The binuclear ruthenium complex dye of the present invention, which has a substituted bipyridyl group, is represented by the formula (1) as described above. The binuclear ruthenium complex dye of the present invention may be preferably (i) a binuclear ruthenium complex dye (also referred to as "binuclear ruthenium complex dye (A)") in which at least one of two

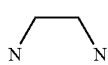

and

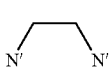

represents a group represented by the formula (2-1) in which n is an integer of from 1 to 4, and R is hydrogen, or a linear or branched alkyl group having 1 to 18 carbon atoms; or (ii) a binuclear ruthenium complex dye (also referred to as "binuclear ruthenium complex dye (B)") in which at least one of two

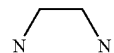

and

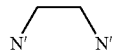

represents a group represented by the formula (2-3); or (iii) a binuclear ruthenium complex dye (also referred to as "binuclear ruthenium complex dye (C)") in which two

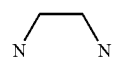

represents a group represented by the formula (2-2), and

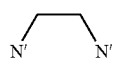

represents a group represented by the formula (2-2) in which $R^1$ and/or $R^2$ is a linear or branched alkyl group having 1 to 30 carbon atoms.

A preferable binuclear ruthenium complex dye (A) may be one in which two

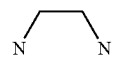

represents a group represented by the formula (2-1) in which n is an integer of from 1 to 4, and R is hydrogen, or a linear or branched alkyl group having 1 to 18 carbon atoms, or a group represented by the formula (2-2), more preferably a group represented by the formula (2-2) in which $R^1$ is a linear or branched alkyl group having 1 to 30 carbon atoms, and $R^2$ is hydrogen, and

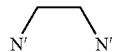

represents a group represented by the formula (2-1) in which n is an integer of from 1 to 4, and R is hydrogen, or a linear or branched alkyl group having 1 to 18 carbon atoms. Another preferable binuclear ruthenium complex dye (A) may be one in which two

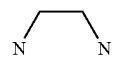

represents a group represented by the formula (2-1) in which n is an integer of from 1 to 4, and R is hydrogen, or a linear or branched alkyl group having 1 to 18 carbon atoms, and

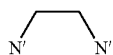

represents a group represented by the formula (2-1) in which n is 0, and R is carboxyl group.

A preferable binuclear ruthenium complex dye (B) may be one in which two

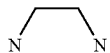

represents a group represented by the formula (2-3), or a group represented by the formula (2-2), more preferably a group represented by the formula (2-2), particularly preferably a group represented by the formula (2-2) in which $R^1$ is hydrogen, and two $R^2$ are joined together to form a benzene ring, and

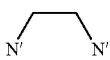

represents a group represented by the formula (2-3). Another preferable binuclear ruthenium complex dye (B) may be one in which two

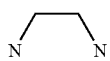

represents a group represented by the formula (2-3), and

represents a group represented by the formula (2-1) in which n is 0, and R is carboxyl group.

Ar in the formula (2-3) may be preferably phenyl group which may have a substituent, and particularly preferably a group represented by the formula (3-1):

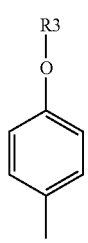

(3-1)

wherein $R^3$ represents a linear or branched alkyl group having 1 to 18 carbon atoms.

A preferable binuclear ruthenium complex dye (C) may be one in which two

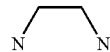

represents a group represented by the formula (2-2), more preferably a group represented by the formula (2-2) in which $R^1$ is a linear or branched alkyl group having 1 to 30 carbon atoms, and $R^2$ is hydrogen, or a group represented by the formula (2-2) in which $R^1$ is hydrogen, and two $R^2$ are joined together to form a benzene ring, and

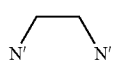

represents a group represented by the formula (2-2) in which $R^1$ is a linear or branched alkyl group having 1 to 30 carbon atoms, and $R^2$ is hydrogen.

In the formula (2-1), Z represents a 5-membered heteroarylene, and may be, for example, thienyl group, furyl group, pyrrolyl group, thiazolyl group, oxazolyl group, imidazolyl group, isothiazolyl group, isoxazolyl group, pyrazolyl group, triazolyl group, oxadiazolyl group, or thiadiazolyl group. Z may be preferably thiazolyl group, for example.

The number of Z may be one, or may be within a range of from two to four, and may be preferably within a range of from one to three, more preferably two. In other words, in the formula (2-1), n may be preferably an integer of from 1 to 3, and more preferably 2. When n is 2 or greater, a plurality of Z may be different from each other. The number of Z may be optionally zero, and may be preferably zero in some cases.

In the formula (2-1), R represents hydrogen, a linear or branched alkyl group having 1 to 18 carbon atoms, or carboxyl group. Two R may be different from each other. R may be preferably hydrogen, or a linear or branched alkyl group having 1 to 18 carbon atoms such as methyl group, ethyl group, propyl group, butyl group, pentyl group, hexyl group, heptyl group, octyl group, nonyl group, decyl group, undecyl group, and dodecyl group, and may be more preferably hydrogen, or a linear or branched alkyl group having 1 to 12 carbon atoms, particularly preferably an alkyl group having 1 to 12 carbon atoms.

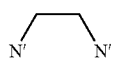

may be particularly preferably a group represented by the formula (2-1) in which n is 0, and R is carboxyl group.

Z may have a substituent other than R. (In other words, any hydrogen atom may be substituted by a substituent.) Examples of the substituent include an alkyl group having 1 to 18 carbon atoms such as methyl group, ethyl group, propyl group, butyl group, pentyl group, hexyl group, heptyl group, octyl group, nonyl group, decyl group, undecyl group, and dodecyl group; an alkoxy group having 1 to 18 carbon atoms such as methoxy group, ethoxy group, propoxy group, butoxy group, pentoxy group, hexyloxy group, heptyloxy group, octyloxy group, nonyloxy group, decyloxy group, undecyloxy group, and dodecyloxy group; an alkylthio group having 1 to 18 carbon atoms such as methylthio group, ethylthio group, propylthio group, butylthio group, pentylthio group, hexylthio group, heptylthio group, octylthio group, nonylthio group, decylthio group, undecylthio group, and dodecylthio group; an N,N-dialkylamino group having 1 to 18 carbon atoms such as N,N-dimethylamino group, N,N-diethylamino group, N,N-dipropylamino group, N,N-dibutylamino group, N,N-dipentylamino group, N,N-dihexylamino group, N,N-diheptylamino group, N,N-dioctylamino group, N,N-dinonylamino group, N,N-didecylamino group, N,N-diundecylamino group, and N,N-didodecylamino group; an N-alkylamino group having 1 to 18 carbon atoms such as N-methylamino group, N-ethylamino group, N-propylamino group, N-butylamino group, N-pentylamino group, N-hexylamino group, N-heptylamino group, N-octylamino group, N-nonylamino group, N-decylamino group, N-undecylamino group, and N-dodecylamino group; an alkylsilyl group having 1 to 18 carbon atoms such as methylsilyl group, ethylsilyl group, propylsilyl group, butylsilyl group, pentylsilyl group, hexylsilyl group, heptylsilyl group, octylsilyl group, nonylsilyl group, decylsilyl group, undecylsilyl group, and dodecylsilyl group; a dialkylsilyl group having 1 to 18 carbon atoms such as dimethylsilyl group, diethylsilyl group, dipropylsilyl group, dibutylsilyl group, dipentylsilyl group, dihexylsilyl group, diheptylsilyl group, dioctylsilyl group, dinonylsilyl group, didecylsilyl group, diundecylsilyl group, and didodecylsilyl group; a trialkylsilyl group having 1 to 18 carbon atoms such as trimethylsilyl group, triethylsilyl group, tripropylsilyl group, tributylsilyl group, tripentylsilyl group, trihexylsilyl group, triheptylsilyl group, trioctylsilyl group, trinonylsilyl group, tridecylsilyl group, triundecylsilyl group, and tridodecylsilyl group; an alkenyl group having 1 to 18 carbon atoms such as ethenyl group, propenyl group, butenyl group, pentenyl group, hexenyl group, heptenyl group, octenyl group, nonenyl group, decenyl group, undecenyl group, and dodecenyl group; an alkynyl group having 1 to 18 carbon atoms such as ethynyl group, propynyl group, butynyl group, pentynyl group, hexynyl group, octynyl group, nonynyl group, decynyl group, undecynyl group, and dodecynyl group; an alkylimino group having 1 to 18 carbon atoms such as methylimino group, ethylimino group, propylimino group, butylimino group, pentylimino group, hexylimino group, heptylimino group, octylimino group, nonylimino group, decylimino group, undecylimino group, and dodecylimino group; hydroxyl group; amino group; mercapto group; halogen atom such as fluoro atom, chloro atom, bromo atom, and iodo atom; and carboxyl group.

The number and position of substituents are not limited, and the adjacent groups may be joined together to form a ring.

In the formula (2-2), $R^1$ and $R^2$ each independently represents hydrogen, or a linear or branched alkyl group having 1 to 30 carbon atoms, preferably an alkyl group having 1 to 18 carbon atoms, or $R^1$ and $R^2$ present on the same pyridine ring or two $R^2$ may be joined together to form a ring. Two $R^1$ may be different from each other, and two $R^2$ may be different from each other.

$R^1$ and $R^2$ may be, for example, hydrogen; methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, or octadecyl group. It is preferred, for example, that $R^1$ is a linear or branched alkyl group having 1 to 18 carbon atoms, more preferably a linear or branched alkyl group having 1 to 12 carbon atoms, and $R^2$ is hydrogen. $R^1$ and $R^2$ may be substituted and may have a substituent as described for Z.

The number and position of substituents are not limited, and the adjacent groups may be joined together to form a ring.

In addition, $R^1$ and $R^2$ present on the same pyridine ring or two $R^2$ may be joined together to form a ring. The formed ring may be, for example, an unconjugated ring such as cyclohexane ring, or a conjugated ring such as benzene ring, naphthalene ring, anthracene ring, and pentacene ring, and may be preferably a conjugated ring, more preferably benzene ring. It is also particularly preferred that $R^1$ is hydrogen, and two $R^2$ are joined together to form a ring, preferably benzene ring, in the formula (2-2). The formed ring may be substituted and may have a substituent as described for Z.

These groups may include various isomers.

In the formula (2-3), Ar represents an aryl group which may have a substituent, and may be, for example, phenyl group, naphthyl group, anthryl group, tetracenyl group, pentacenyl group, azulenyl group, fluorenyl group, phenanthrenyl group, triphenylenyl group, pyrenyl group, chrysenyl group, picenyl group, perylenyl group, pentaphenyl group, or dibenzophenanthrenyl group. Ar may be preferably a substituted or unsubstituted phenyl group, for example. Two Ar may be different from each other.

Ar may have a substituent. (In other words, any hydrogen atom may be substituted by a substituent.) Examples of the substituent include substituents as described for Z. The number and position of substituents are not limited, and the adjacent groups may be joined together to form a ring.

Ar may be particularly preferably, for example, a group represented by the formula (3-1):

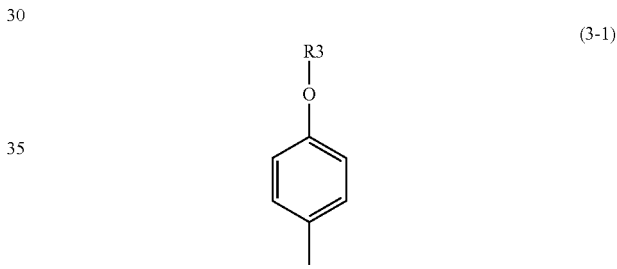

(3-1)

wherein R3 represents a linear or branched alkyl group having 1 to 18 carbon atoms.

R3 may be, for example, methyl group, ethyl group, propyl group, butyl group, pentyl group, hexyl group, heptyl group, octyl group, nonyl group, decyl group, undecyl group, or dodecyl group, and may be preferably a linear or branched alkyl group having 1 to 12 carbon atoms, more preferably a linear or branched alkyl group having 1 to 6 carbon atoms.

In the formula (1), X represents a counter ion. X may be, for example, hexafluorophosphate ion, perchlorate ion, tetraphenylborate ion, tetrafluoroborate ion, trifluoromethanesulfonate ion, thiocyanate ion, sulfate ion, nitrate ion, or halide ion, and may be preferably hexafluorophosphate ion, tetrafluoroborate ion, trifluoromethanesulfonate ion, nitrate ion or halide ion, and more preferably hexafluorophosphate ion, tetrafluoroborate ion, nitrate ion or iodide ion. In addition, m represents a number of the counter ions needed to neutralize a charge of the complex.

The binuclear ruthenium complex dye of the present invention (binuclear ruthenium complex dye (A)), which has a bipyridyl group substituted with a 5-membered heteroaryl group, may be prepared by reacting two different mononuclear ruthenium complexes as shown in the following scheme, for example, by reference to WO2006/038587.

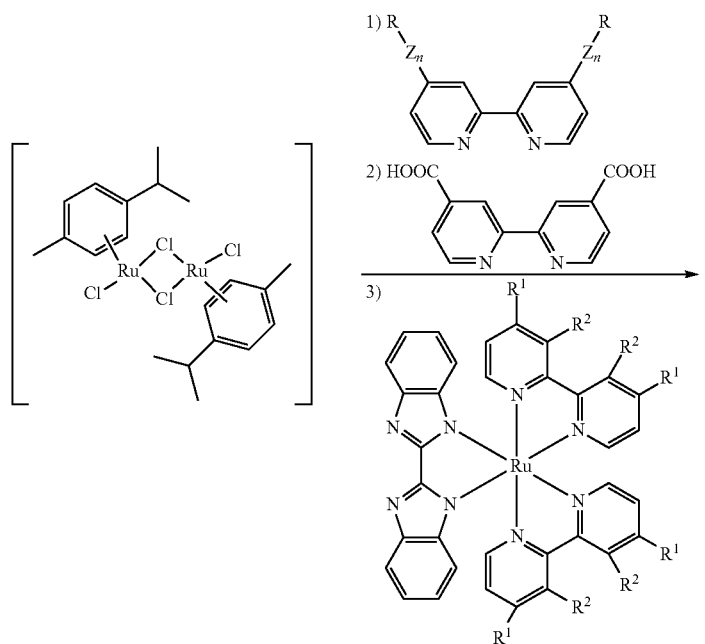
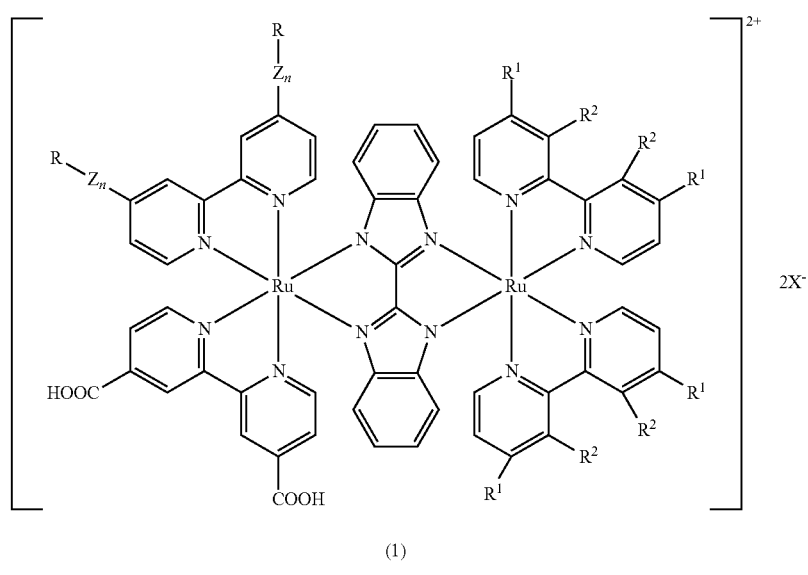
wherein Z, n, R, $R^1$ and $R^2$ are defined as above, and $X^-$ represents a monovalent anion being a counter ion.

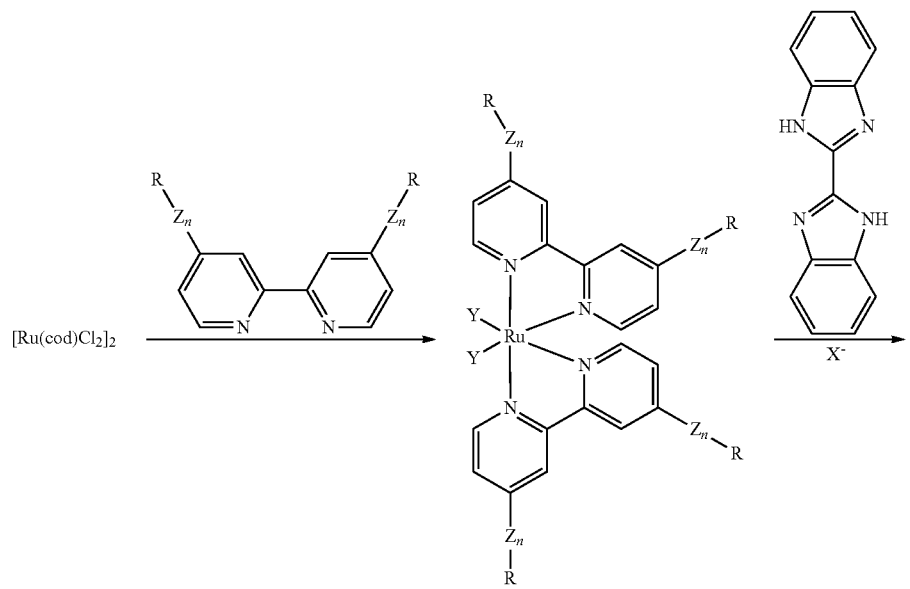
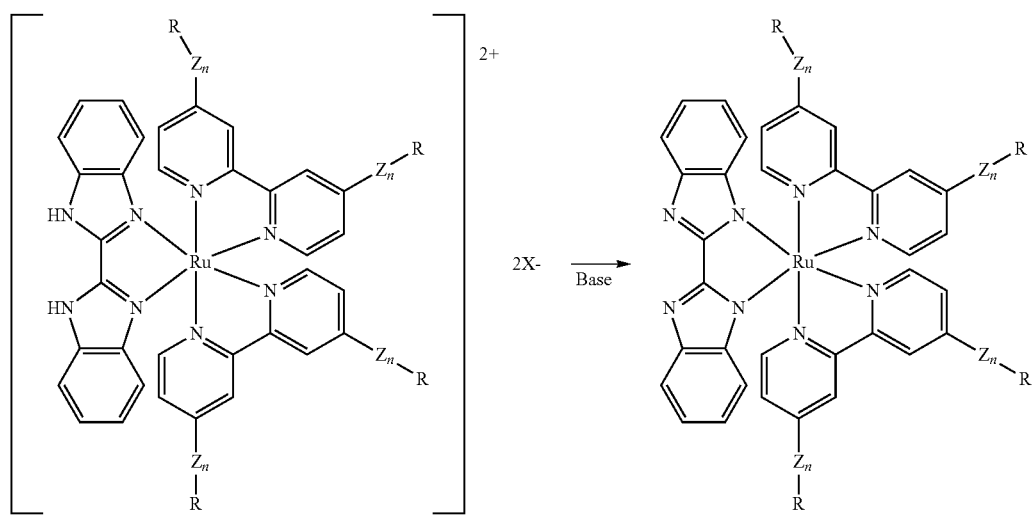
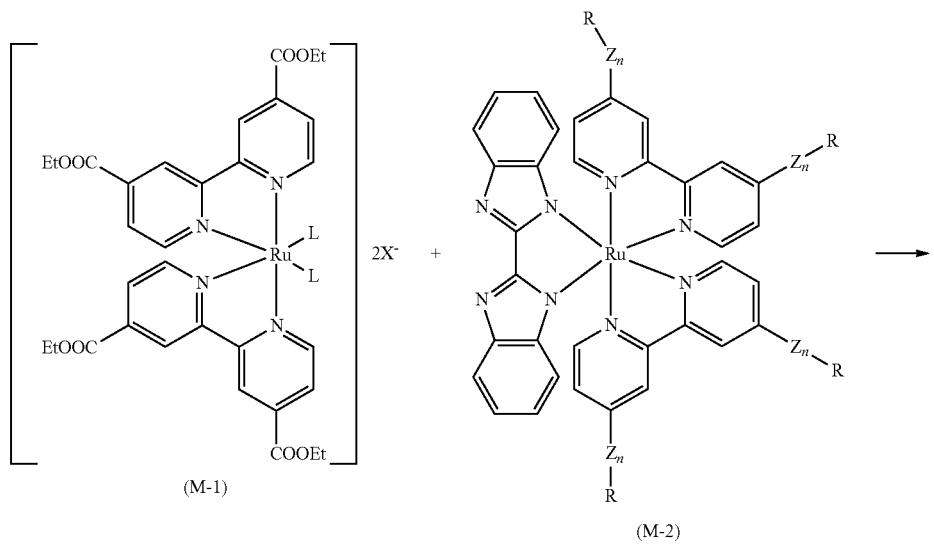

-continued
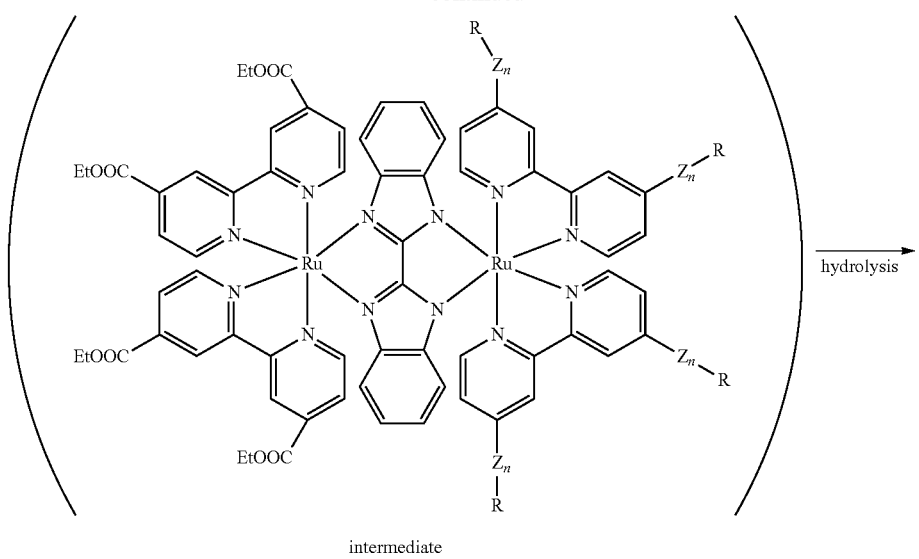
intermediate
$\xrightarrow{\text{hydrolysis}}$
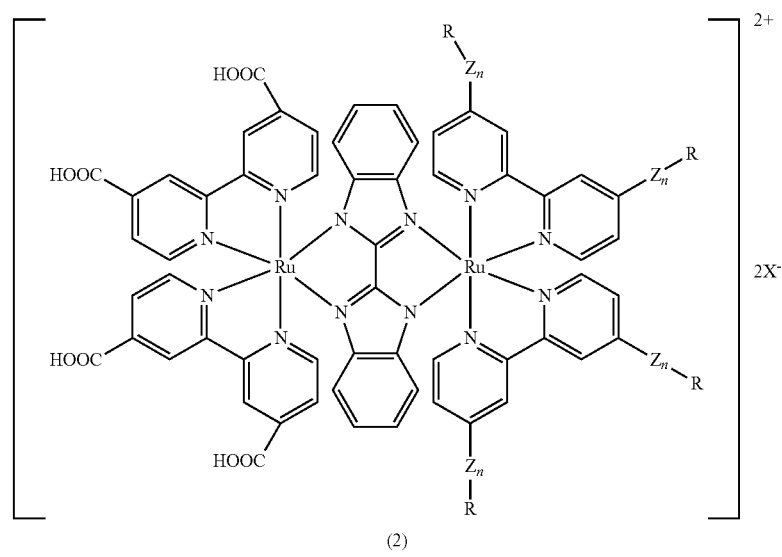
(2)

wherein Z, n and R are defined as above, and X⁻ represents a monovalent anion being a counter ion, Y represents a halogen atom, and L represents a neutral molecule, including water molecule and an organic solvent molecule such as acetone. In addition, "cod" stands for 1,5-cyclooctadiene.

The counter ion (X) is not limited to a monovalent anion, and other complex dyes may be synthesized in the same way as described above.

The binuclear ruthenium complex dye of the present invention (binuclear ruthenium complex dye (B)), which has a bipyridyl group substituted with a unsaturated group, may be prepared by reacting two different mononuclear ruthenium complexes as shown in the following scheme, for example.

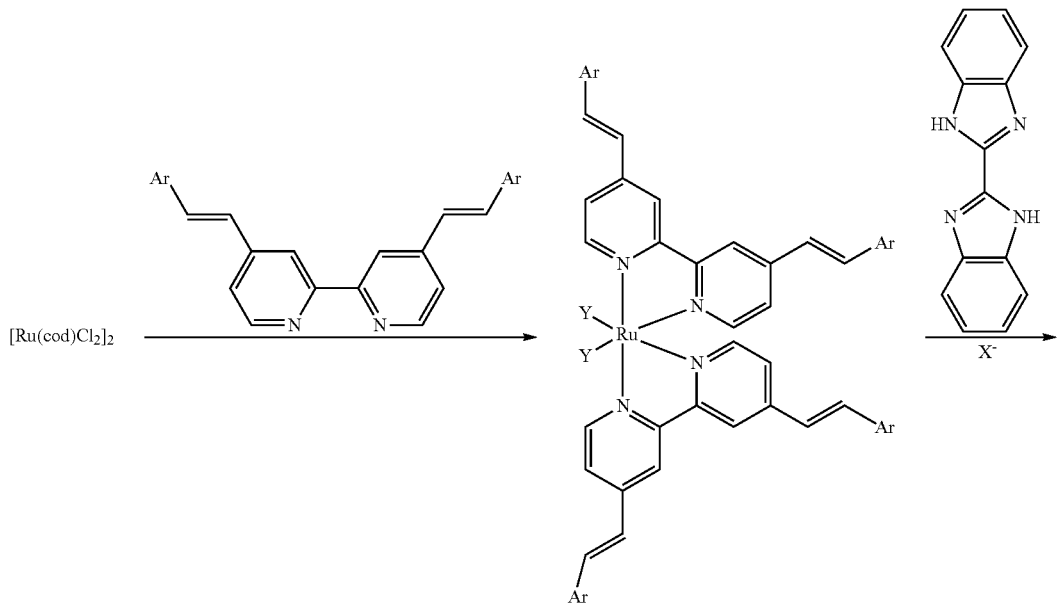

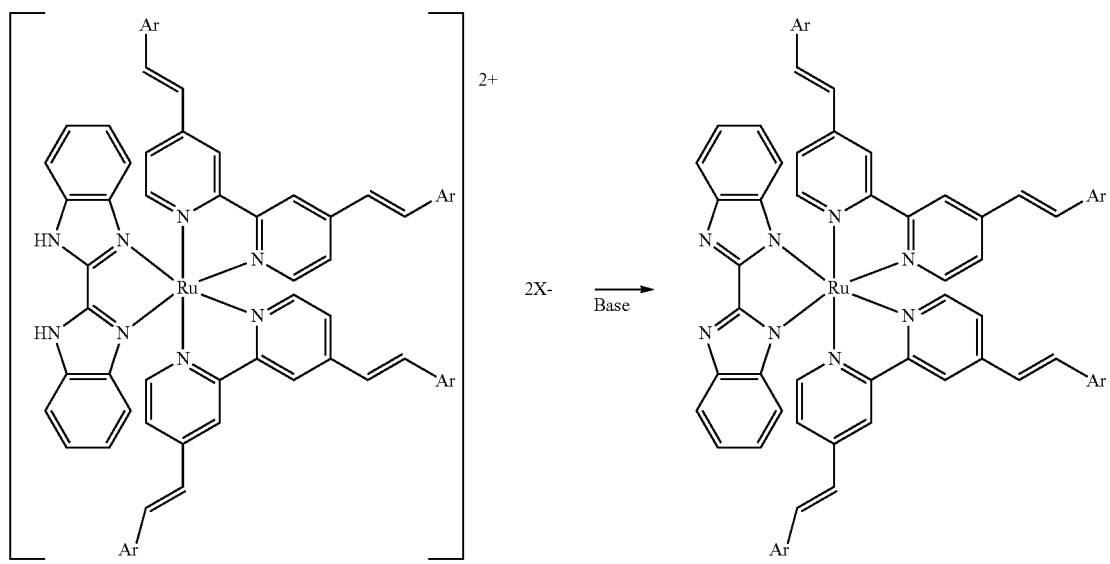

-continued
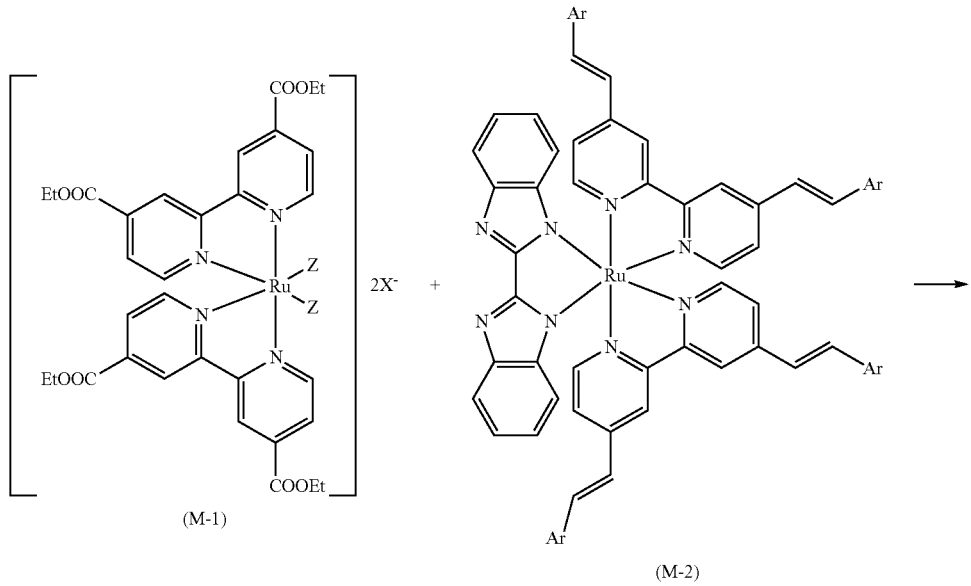
(M-1)　(M-2)
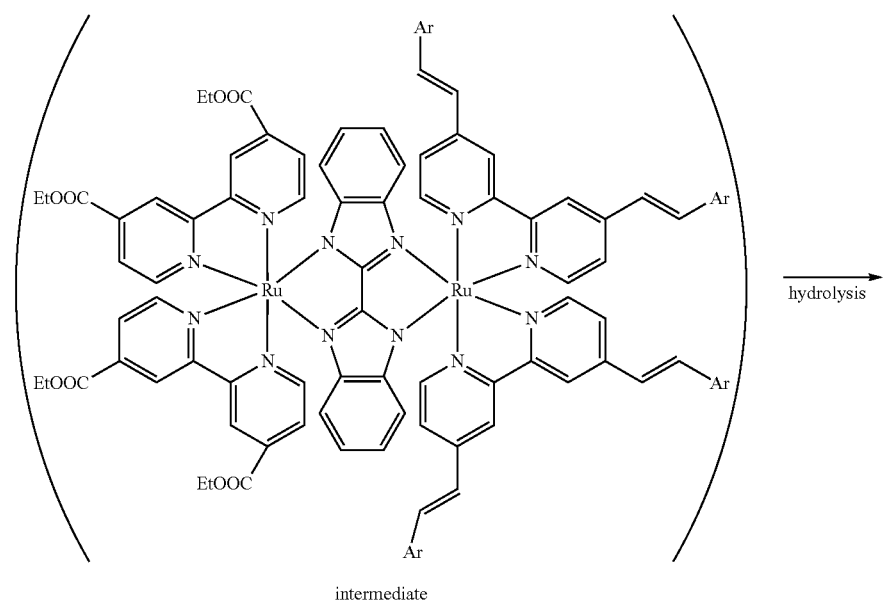
intermediate

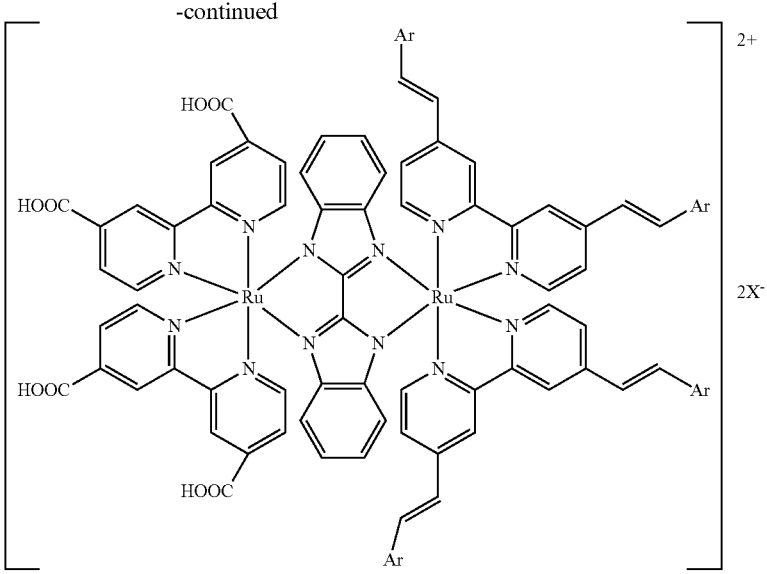

(1)

wherein Ar is defined as above, and X⁻ represents a monovalent anion being a counter ion, Y represents a halogen atom, and Z represents a neutral molecule. In addition, "cod" stands for 1,5-cyclooctadiene.

The counter ion (X) is not limited to a monovalent anion, and other complex dyes may be synthesized in the same way as described above.

One of the mononuclear ruthenium complexes may be synthesized via a mononuclear ruthenium complex precursor. The synthetic intermediate, i.e. the mononuclear ruthenium complex represented by the formula (2):

and the mononuclear ruthenium complex represented by the formula (3):

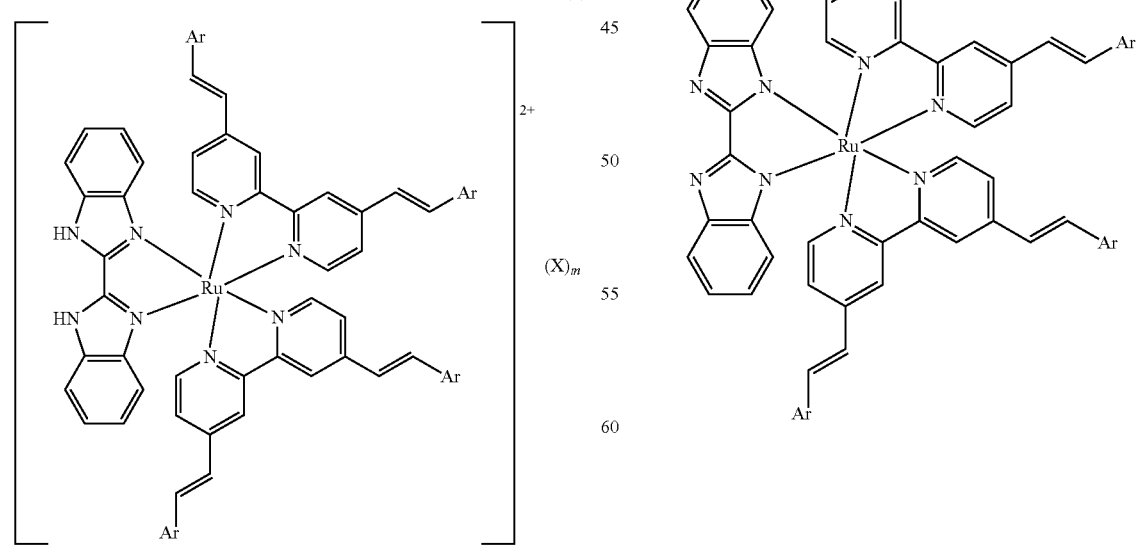

wherein Ar, X and m are defined as above, wherein Ar is defined as above, are novel compounds.

The compound represented by the formula (3) may have a NH-proton, as represented by the formula (4):

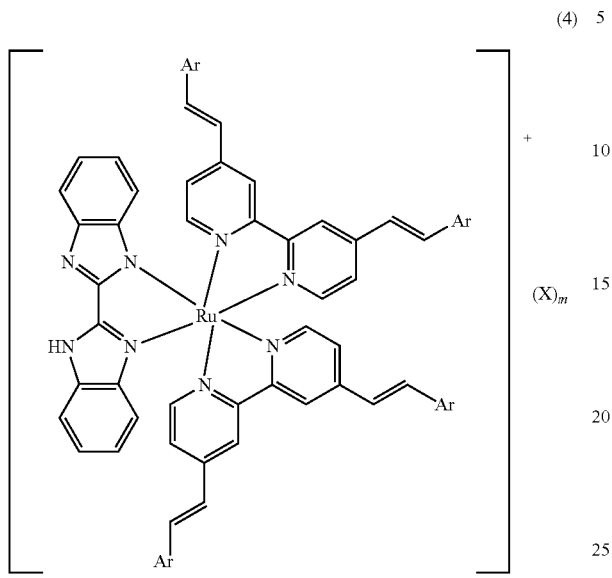

(4)

wherein Ar, X and m are defined as above.

In another embodiment, the binuclear ruthenium complex dye of the present invention (binuclear ruthenium complex dye (B)), which has a bipyridyl group substituted with a unsaturated group, may be prepared by reacting two different mononuclear ruthenium complexes as shown in the following scheme, for example.

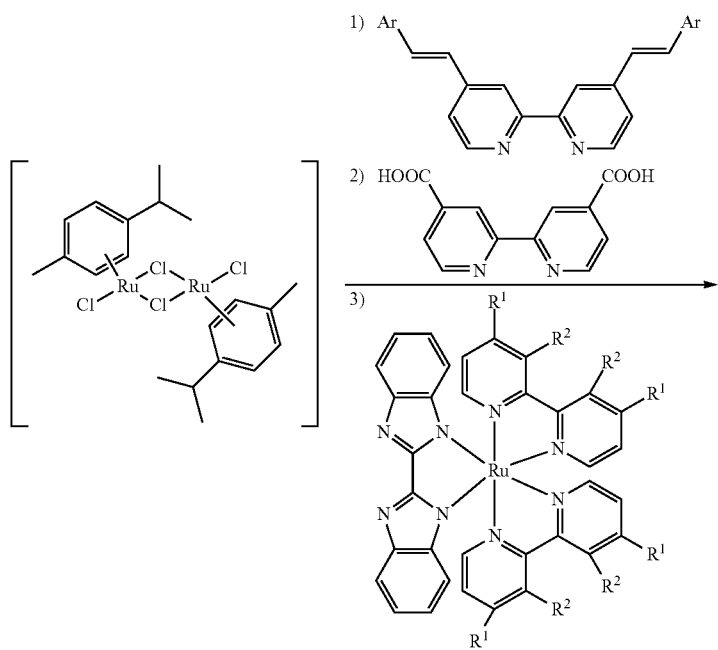

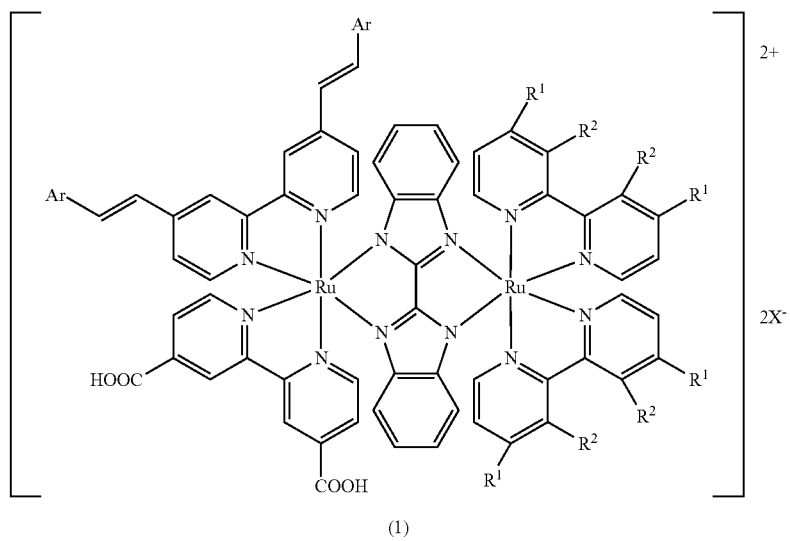

(1)

wherein Ar, $R^1$ and $R^2$ are defined as above, and $X^-$ represents a monovalent anion being a counter ion.

The counter ion (X) is not limited to a monovalent anion, and other complex dyes may be synthesized in the same way as described above.

The binuclear ruthenium complex dye of the present invention (binuclear ruthenium complex dye (C)), which has a substituted bipyridyl group, may be prepared by reacting [Ru(p-cymene)Cl$_2$]$_2$ with a ligand and a mononuclear ruthenium complex successively as shown in the following scheme, for example.

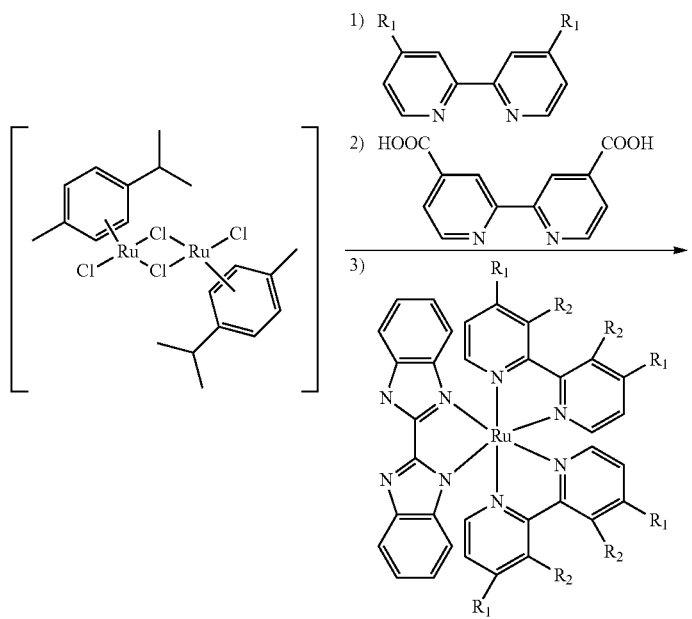

-continued

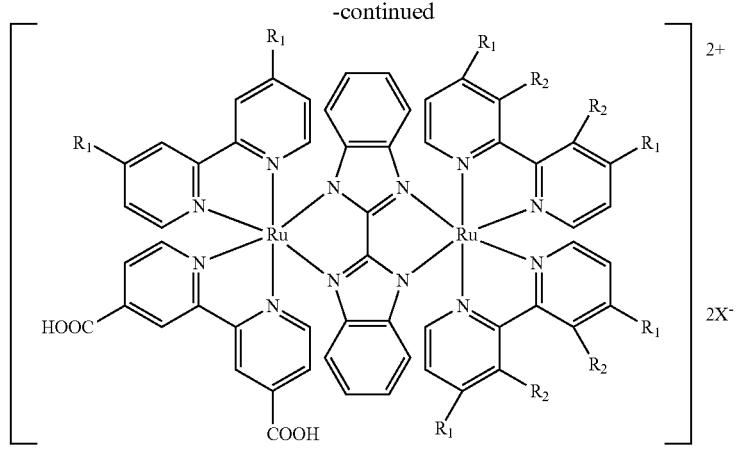

wherein $R^1$ and $R^2$ are defined as above, and $X^-$ represents a monovalent anion being a counter ion.

The counter ion (X) is not limited to a monovalent anion, and other complex dyes may be synthesized in the same way as described above.

In the binuclear ruthenium complex dye of the present invention, which has a substituted bipyridyl group, proton(s) (H+) of one or more carboxyl groups (—COOH) may dissociate. The dissociation of proton (H+) may be achieved mainly by adjusting the pH of the binuclear ruthenium complex dye solution.

The photoelectric conversion element of the present invention comprises the binuclear ruthenium complex dye as described above, and a semiconductor particle. The binuclear ruthenium complex dye is adsorbed on the surface of the semiconductor particle, and the semiconductor particle is sensitized with the ruthenium complex dye.

More specifically, the photoelectric conversion element of the present invention comprises a semiconductor particle sensitized with the ruthenium complex dye, which is fixed on a conductive support (electrode).

The conductive electrode may be preferably a transparent electrode, which is formed on a transparent substrate. Examples of a conducting agent include metals such as gold, silver, copper, platinum and palladium; indium oxide-based compounds, typified by tin-doped indium oxide (ITO); tin oxide-based compounds, typified by fluorine-doped tin oxide (FTO); and zinc oxide-based compounds.

Examples of the semiconductor particle include titanium oxide, zinc oxide and tin oxide. The other examples may include indium oxide; niobium oxide; tungsten oxide; vanadium oxide; composite oxide semiconductors such as strontium titanate, calcium titanate, barium titanate and potassium niobate; cadmium or bismuth sulfide; cadmium selenide or telluride; and gallium phosphide or arsenide. The semiconductor particle may be preferably an oxide, particularly preferably titanium oxide, zinc oxide, tin oxide, or a mixture comprising at least one of these oxides, for example.

A primary particle size of the semiconductor particle is generally, but not limited to, from 1 nm to 5,000 nm, preferably from 2 nm to 500 nm, particularly preferably from 5 nm to 400 nm.

The binuclear ruthenium complex dye may be adsorbed onto a semiconductor particle, for example, by forming a semiconductor layer which comprises a semiconductor particle (semiconductor particle film) on a conductive support; and then immersing the semiconductor layer in a solution containing the binuclear ruthenium complex dye. The semiconductor layer may be formed by applying a paste of semiconductor particle onto a conductive support; and then calcining the paste. Subsequently, the conductive support on which the semiconductor layer is formed is immersed in a dye solution, and then the conductive support is washed and dried.

Examples of a solvent for the dye solution include water; alcohols such as methanol, ethanol, isopropyl alcohol, t-butyl alcohol and ethylene glycol; nitriles such as acetonitrile and propionitrile; amides such as N,N-dimethylacetamide and N,N-dimethylformamide; ureas such as N-methylpyrrolidone; and sulfoxides such as dimethylsulfoxide. The solvent to be used may be preferably water, an alcohol or a nitrile, more preferably water, ethanol, isopropyl alcohol, t-butanol or acetonitrile. These solvents may be used alone or in combination of two or more.

The concentration of the dye in the solution may be preferably from 0.001 mmol/l to the saturation concentration of the complex dye of the present invention, more preferably from 0.001 mmol/l to 100 mmol/l, particularly preferably from 0.01 mmol/l to 10 mmol/l, and more preferably from 0.05 mmol/l to 1.0 mmol/l.

The dye solution may contain a compound having a steroid skeleton such as cholic acid, deoxycholic acid and chenodeoxycholic acid.

The temperature at which the dye is adsorbed onto a semiconductor particle is generally from 0° C. to 80° C., preferably from 20° C. to 40° C. The time period for which the dye is adsorbed onto a semiconductor particle (time period for which a semiconductor particle is immersed in the dye solution) may be appropriately selected depending on the type of the binuclear ruthenium complex dye, the concentration of the dye in the solution, and other conditions.

The photochemical cell of the present invention comprises the photoelectric conversion element of the present invention as described above. More specifically, the photochemical cell comprises the photoelectric conversion element of the present invention as described above, and a counter electrode as electrodes; and comprises an electrolyte layer between the electrodes. At least one of the electrodes, which are the photoelectric conversion element of the present invention and the counter electrode, is a transparent electrode.

The counter electrode functions as a cathode when it is combined with the photoelectric conversion element to form a photochemical cell. Although the counter electrode to be used may be a substrate on which a conductive layer is formed, like the conductive electrode as described above, the counter electrode may be a metal plate by itself and does not necessarily need a substrate. Examples of a conducting agent to be used for the counter electrode include metals such as platinum and carbon; and conductive metal oxides such as fluorine-doped tin oxide.

The electrolyte (redox couple) may be selected from any known materials without limitations. Examples of the electrolyte to be used include a combination of iodine and an iodide (for example, metal iodides such as lithium iodide and potassium iodide, or iodides of a quaternary ammonium compound such as tetrabutylammonium iodide, tetrapropylammonium iodide, pyridinium iodide and imidazolium iodide); a combination of bromine and a bromide; a combination of chlorine and a chloride; a combination of an alkylviologen and a reductant thereof, quinone/hydroquinone; transition metal ion pair such as iron (II) ion/iron (III) ion, copper (I) ion/copper (II) ion, manganese (II) ion/manganese (III) ion, and cobalt (II) ion/cobalt (III) ion; a combination of complex ions such as ferrocyanide/ferricyanide, cobalt (II) tetrachloride/cobalt (III) tetrachloride, cobalt (II) tetrabromide/cobalt (III) tetrabromide, iridium(II) hexachloride/iridium (III) hexachloride, ruthenium (II) hexacyanide/ruthenium (III) hexacyanide, rhodium(II) hexachloride/rhodium(III) hexachloride, rhenium (III) hexachloride/rhenium (IV) hexachloride, rhenium (IV) hexachloride/rhenium (V) hexachloride, osmium (III) hexachloride/osmium (IV) hexachloride, and osmium (IV) hexachloride/osmium (V) hexachloride; complexes formed with a transition metals such as cobalt, iron, ruthenium, manganese, nickel and rhenium, and a conjugated heterocyclic ring or derivative thereof such as bipyridine or derivative thereof, terpyridine or derivative thereof, and phenanthroline or derivative thereof; complexes of cyclopentadiene or derivative thereof and a metal such as ferrocene/ferrocenium ion, cobaltocene/cobaltocenium ion, and ruthenocene/ruthenocenium ion; and porphyrin compounds. A preferable electrolyte may be a combination of iodine and lithium iodide or an iodide of a quaternary ammonium compound. The electrolyte may be a liquid in which the electrolyte is dissolved in an organic solvent, a molten salt, a so-called gel electrolyte in which the electrolyte is impregnated in a polymer matrix, or a solid electrolyte.

Examples of a solvent for the electrolyte solution to be used include, but not limited to, water, alcohols, nitriles, chain ethers, cyclic ethers, chain esters, cyclic esters, chain amides, cyclic amides, chain sulfones, cyclic sulfones, chain ureas, cyclic ureas, and amines. These solvents may be used alone or in combination of two or more.

The photochemical cell of the present invention may be produced by any conventional process.

For example, the photochemical cell of the present invention may be produced as follows. As described above, a paste of semiconductor particle such as an oxide is applied onto a transparent electrode, and then calcined, to form a semiconductor particle film. In the case where the semiconductor particle film is formed of titania, the paste is calcined at a temperature of from 450° C. to 500° C. for 30 minutes, for example. The transparent electrode with the semiconductor particle film is immersed in a dye solution (a solution containing the binuclear ruthenium complex dye of the present invention) to fix the dye on the semiconductor particles, thereby producing a photoelectric conversion element. Then, the photoelectric conversion element is combined with a transparent electrode on which platinum or carbon is vapor-deposited as a counter electrode, and an electrolyte is placed between them, to produce the photochemical cell of the present invention.

EXAMPLES

The present invention will be described in more detail below with reference to the Examples. However, the scope of the present invention should not be limited to the Examples.

Abbreviations in the Examples are as follows:
bpy; 2,2'-bipyridine,
dnbpy; 4,4'-dinonyl-2,2'-bipyridine,
$H_2$dcbpy; 2,2'-bipyridine-4,4'-dicarboxylic acid,
Etcbpy; 2,2'-bipyridine-4,4'-dicarboxylic acid diethyl ester,
BiBzImH$_2$, BiBzIm; 2,2'-bibenzimidazole,
BiHeBiTbpy; 4,4'-bis(5'-hexyl-[2,2"bithiophene]-5-yl)-2,2'-bipyridine,
BiHexoStbpy; 4,4'-bis(4-(hexyloxy)styryl)-2,2'-bipyridine,
phen; 1,10-phenanthroline,
OTf; trifluoromethane sulfonate ion,
cod; 1,5-cyclooctadiene.

Binuclear Ruthenium Complex Dye (A)

Example A1

(Synthesis of the Binuclear Ruthenium Complex Dye (1a))

Under argon atmosphere, into a 200 mL three-necked flask were placed dichloro-p-cymene ruthenium dimer (0.100 g, 0.163 mmol), BiHeBiTbpy (0.214 g, 0.328 mmol) and N,N-dimethylformamide (50 mL). After deaeration, the mixture was reacted at 60° C. for 4 hours.

The reaction solution was cooled down, and then H₂dcbpy (0.08 g, 0.328 mmol) was added to the reaction solution. After re-deaeration, the mixture was reacted at 140° C. for 21.5 hours. The reaction solution was cooled down, and then sodium hydroxide (0.030 g) and [Ru(dnbpy)₂(BiBzIm)] (0.330 g, 0.294 mmol) were added to the reaction solution, and the mixture was reacted at 140° C. for 6.5 hours.

The resultant reaction solution was filtrated, and the filtrate was concentrated under reduced pressure. And then, acetone (30 mL) and a hexafluorophosphoric acid aqueous solution at pH 2.4 (90 mL) were added to the resultant concentrate, and the mixture was stirred at room temperature for 1 hour. And then, the precipitate was collected by filtration, and washed with a mixture of acetone and hexafluorophosphoric acid aqueous solution at pH 2.4 (1:3), to provide the binuclear ruthenium complex dye (1a) (0.610 g).

The representative structure of the binuclear ruthenium complex dye is shown as the formula (1a). In the complex dye, one or more protons of carboxyl groups may dissociate.

Example A2

Synthesis of the Binuclear Ruthenium Complex Dye (2a)

Example A2-A

Synthesis of the Mononuclear Ruthenium Complex (M-1); [Ru(Etcbpy)₂(H₂O)₂](OTf)₂

Under nitrogen atmosphere, into a 500 mL three-necked flask were placed commercially available H₂dcbpy (5.44 g, 22.3 mmol), concentrated sulfuric acid (10 mL) and ethanol (130 mL). The mixture was refluxed and reacted overnight. The reaction solution was cooled down, and then the reaction solution was neutralized. The precipitate was collected by filtration, and washed with hot water. And then, the precipitate was recrystallized with ethanol/water (95:5). The resultant crystal was collected by filtration, and then dried under vacuum, to provide Etcbpy (4.92 g).

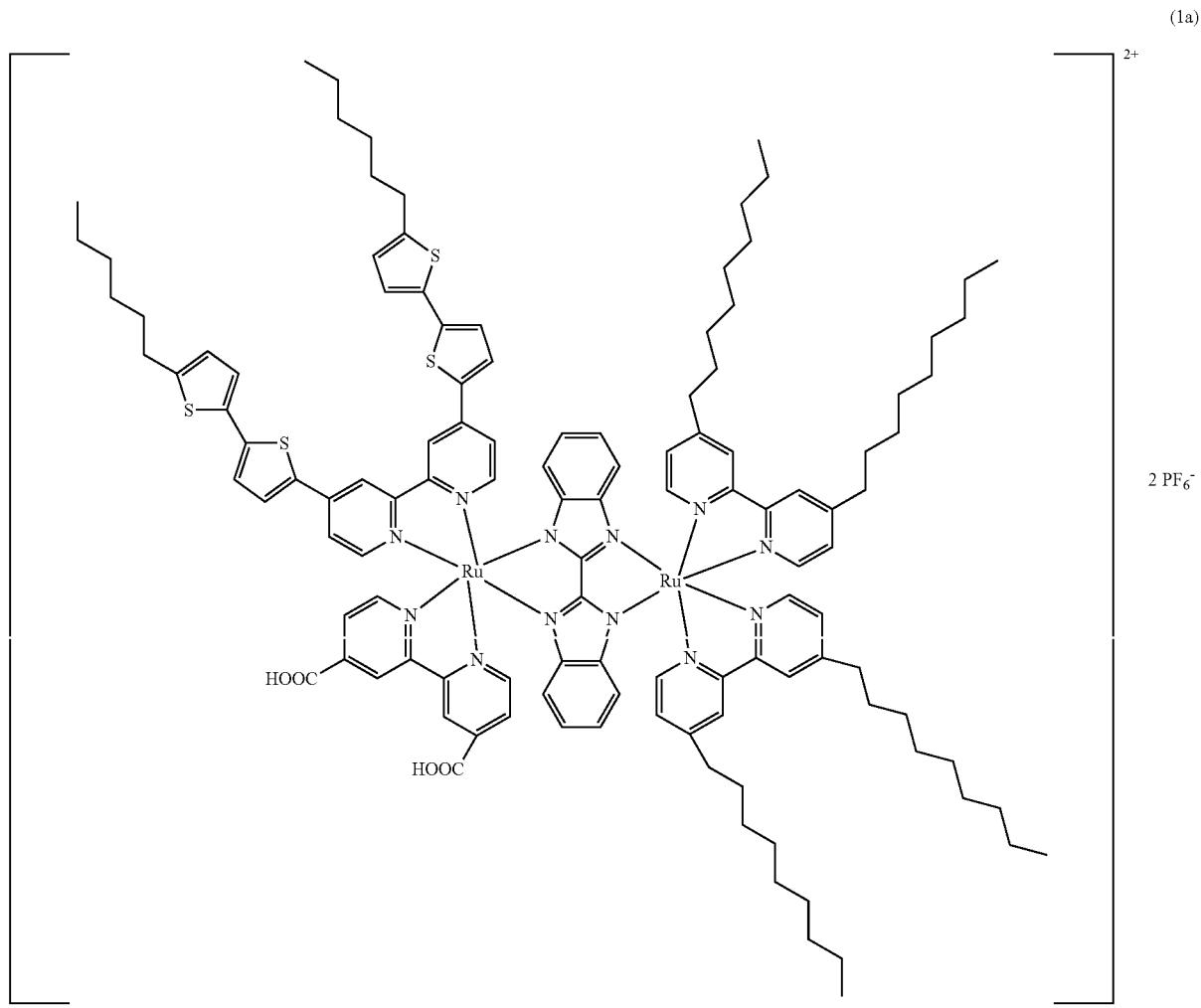

Subsequently, under argon atmosphere, into a 1000 mL three-necked flask were placed commercially available ruthenium chloride (1.18 g, 4.51 mmol), Etcbpy (2.64 g, 8.79 mmol) and ethanol (500 mL). The mixture was refluxed and reacted for 7 hours. The reaction solution was cooled down, and then the precipitate was collected by filtration, and dried under vacuum, to provide [Ru(Etcbpy)$_2$Cl$_2$] (1.64 g). In addition, the resultant filtrate was concentrated under reduced pressure. And then, a 2 mol/L hydrochloric acid (300 mL) was added to the resultant concentrate, and the mixture was stirred at room temperature for 5 minutes. After completion of stirring, the precipitate was collected by filtration, and washed with water. And then, the insoluble substance was recrystallized with ethanol/dichloromethane (10:3). The resultant crystal was collected by filtration, and then dried under vacuum, to provide [Ru(Etcbpy)$_2$Cl$_2$] (1.34 g). Consequently, 2.98 g of [Ru(Etcbpy)$_2$Cl$_2$] was obtained in total.

Subsequently, into a 200 mL three-necked flask were placed [Ru(Etcbpy)$_2$Cl$_2$] (1.37 g, 1.77 mmol), silver trifluoromethane sulfonate (1.09 g, 4.25 mmol) and dichloromethane (140 mL). The mixture was stirred at room temperature for 1 hour. After allowing the reaction solution to stand overnight, the reaction solution was filtrated, and the filtrate was concentrated under reduced pressure. And then, diethyl ether was added to the resultant concentrate, and the mixture was stirred at room temperature for 5 minutes. After completion of stirring, the precipitate was collected by filtration, and washed with diethyl ether, and then dried under vacuum, to provide [Ru(Etcbpy)$_2$(H$_2$O)$_2$](OTf)$_2$ (1.62 g).

Example A2-B

Synthesis of the Mononuclear Ruthenium Complex (M-2); [(BiBzIm)Ru(BiHeBiTbpy)$_2$]

Into a 200 mL three-necked flask were placed BiHeBiTbpy (0.375 g, 0.574 mmol), [Ru(cod)Cl$_2$]$_n$ (0.096 g, 0.344 mmol) and N,N-dimethylacetamide (36 mL). After deaeration, the mixture was refluxed for 24 minutes while being stirred under irradiation with 2.45 GHz microwave. The reaction solution was cooled down, and then the precipitate was collected by suction filtration, and washed with N,N-dimethylacetamide, and then dried under vacuum, to provide [Ru(BiHeBiTbpy)$_2$Cl$_2$] (0.371 g).

Subsequently, under argon atmosphere, into a 100 mL three-necked flask were placed Ru(BiHeBiTbpy)$_2$Cl$_2$ (0.357 g, 0.242 mmol), BiBzImH$_2$ (0.062 g, 0.266 mmol) and N,N-dimethylacetamide (25 mL). After deaeration, the mixture was intermittently refluxed for 98 minutes while being stirred under irradiation with 2.45 GHz microwave. The reaction solution was cooled down, and then filtrated. And then, water (12 mL) and ammonium hexafluorophosphate (0.158 g, 0.097 mmol) dissolved in water (1 mL) were added to the resultant filtrate. The resultant mixture was stirred at room temperature for 1 hour. After completion of stirring, the suspension was filtrated. The collected precipitate was washed with a mixture of N,N-dimethylacetamide and water (20:12), and then dried under vacuum, to provide [Ru(BiHeBiTbpy)$_2$BiBzImH$_2$](PF$_6$)$_2$ (0.166 g).

Subsequently, into a 100 mL three-necked flask were placed [Ru(BiHeBiTbpy)$_2$BiBzImH$_2$](PF$_6$)$_2$ (0.149 g, 0.077 mmol), methanol (5 mL) and a 28% sodium methoxide methanol solution (0.15 mL, 0.77 mmol). After deaeration, the mixture was refluxed for 2 hours. The reaction solution was cooled down, and then filtrated. The collected precipitate was washed with a sodium methoxide methanol solution which had the same concentration as the reaction solution, and then dried under vacuum, to provide the mononuclear ruthenium complex (M-2) [Ru(BiHeBiTbpy)$_2$(BiBzIm)] (0.133 g).

Example A2-C

Synthesis of the Binuclear Ruthenium Complex dye (2a)

Under argon atmosphere, into a 20 mL Schlenk flask were placed the mononuclear ruthenium complex (M-1) (0.038 g, 0.038 mmol), the mononuclear ruthenium complex (M-2) (0.059 g, 0.036 mmol) and N,N-dimethylacetamide (12.5 mL). After deaeration, the mixture was refluxed for 24 minutes while being stirred under irradiation with 2.45 GHz microwave. The resultant reaction solution was filtrated, and the filtrate was concentrated under reduced pressure. And then, a 0.2 mol/L sodium hydroxide aqueous solution (16.3 mL) was added to the resultant concentrate, and the mixture was heated at 100° C. for 2 hours. The reaction solution was cooled down, and then filtrated. And then, methanol (7.5 mL), water (7.5 mL) and a 1 mol/L sodium hydroxide aqueous solution (0.02 mL) were added to the collected precipitate. The resultant mixture was stirred with ultrasonic for 15 minutes. And then, a 0.72 mol/L hexafluorophosphoric acid aqueous solution was added to the resultant mixture until pH became 3.8. After allowing the mixture to stand overnight, the precipitate was collected by filtration, and washed with a hexafluorophosphoric acid aqueous solution at pH 3.8 and a mixture of acetone and diethyl ether (1:8), and then dried under vacuum. Subsequently, methanol (12 mL), water (12 mL) and a 1 mol/L sodium hydroxide aqueous solution (0.02 mL) were added to the collected precipitate. The resultant mixture was stirred with ultrasonic for 15 minutes. And then, a 0.72 mol/L hexafluorophosphoric acid aqueous solution was added to the resultant mixture until pH became 2.8. After allowing the mixture to stand overnight, the precipitate was collected by filtration, and washed with a hexafluorophosphoric acid aqueous solution at pH 2.8, to provide the binuclear ruthenium complex dye (2a) (0.034 g).

The representative structure of the binuclear ruthenium complex dye is shown as the formula (2a). In the complex dye, one or more protons of carboxyl groups may dissociate.

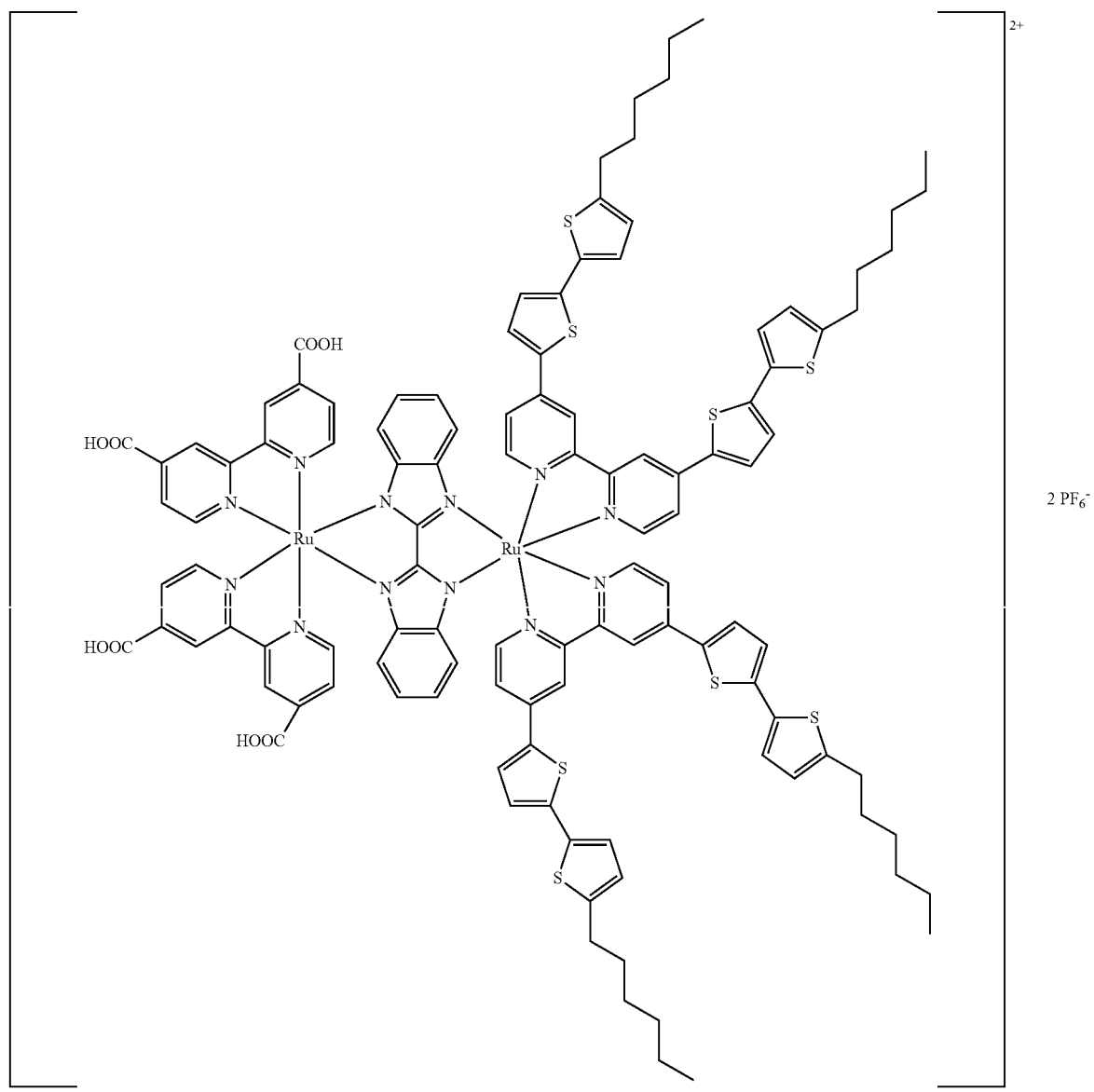
(2a)
Reference Example A1
Synthesis of the Conventional Binuclear Ruthenium Complex Dye (3)
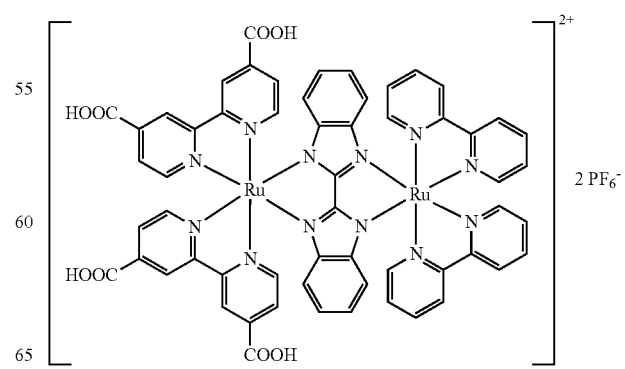
(3)
The binuclear ruthenium complex dye (3) was synthesized according to a known method.

Example A3-1

Production of a Porous Titania Electrode

A titania paste PST-18NR for a transparent layer and a titania paste PST-400C for a diffusion layer, both of which were made by Catalysts & Chemicals Industries Co., Ltd., were applied onto a transparent conductive glass electrode, which was made by Asahi Glass Co., Ltd., using a screen printer. The film thus obtained was aged in an atmosphere at 25° C. and 60% RH for 5 minutes, and then the aged film was calcined at 450° C. for 30 minutes. After the film was cooled down, the same procedure was repeated to achieve the predetermined thickness, thereby producing a 16 $mm^2$ porous titania electrode.

Example A3-2

Production of a Dye-Adsorbed Porous Titania Electrode

The porous titania electrode was immersed in a 0.2 mmol/L binuclear ruthenium complex dye solution [solvent: mixed solvent of t-butanol and acetonitrile (1:1)] at 30° C. for the predetermined time period, and then the electrode was dried, to provide a dye-adsorbed porous titania electrode.

Example A3-3

Production of a Photochemical Cell

The dye-adsorbed porous titania electrode thus obtained was placed on a platinum plate (counter electrode). Subsequently, an electrolyte (a solution prepared by dissolving lithium iodide, iodine, 4-t-butylpyridine and 1,2-dimethyl-3-propylimidazolium iodide in 3-methoxypropionitrile in an amount of 0.1 mol/L, 0.05 mol/L, 0.5 mol/L and 0.6 mol/L, respectively) was poured into a gap between these electrodes by the capillary action, to provide a photochemical cell.

Example A4

Measurement of Ultraviolet-Visible Absorption Spectrum

Three different types of $3\times10^{-5}$ mol/l solutions of the following complexes in ethanol were prepared, and ultraviolet-visible absorption spectra of the solutions were measured.
(1) Binuclear ruthenium complex of the present invention (1a; prepared in Example A1)
(2) Binuclear ruthenium complex of the present invention (2a; prepared in Example A2)
(3) Conventional binuclear ruthenium complex (3; prepared in Reference Example A1).

Figure 2:
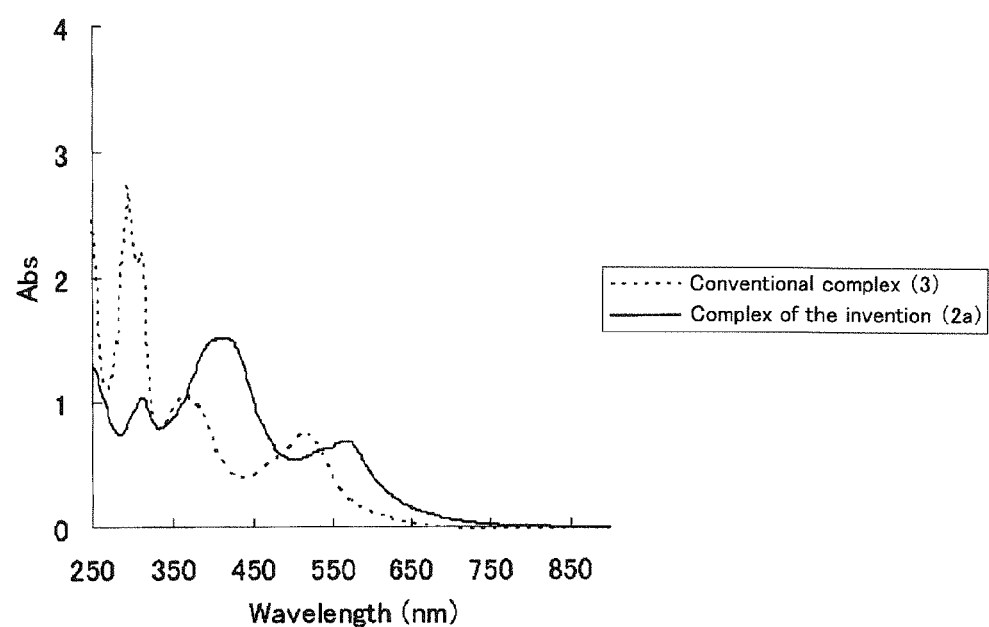
FIG. 2 is ultraviolet-visible absorption spectra of the binuclear ruthenium complex (2a) and the conventional binuclear ruthenium complex (3).

FIG. 1 and FIG. 2 show ultraviolet-visible absorption spectra of the binuclear ruthenium complex (1a) and the binuclear ruthenium complex (3), and ultraviolet-visible absorption spectra of the binuclear ruthenium complex (2a) and the binuclear ruthenium complex (3), respectively.

The complex (binuclear ruthenium complex dye) of the present invention, i.e. the complex (1a) which is substituted with [2,2'-bithiophene]-5-yl groups at the 4- and 4'-positions on 2,2'-bipyridine ring, had a light absorption wavelength range shifted by about 40 nm to longer wavelength and had an absorbance of the longest wavelength peak 1.3 times higher under the same concentration conditions, as compared with the known binuclear ruthenium complex (3) which is unsubstituted at the 4- and 4'-positions. The complex (2a) of the present invention had a light absorption wavelength range shifted by about 58 nm to longer wavelength and had a significantly greater absorbance around the range of from 350 nm to 450 nm, as compared with the known binuclear ruthenium complex (3) which is unsubstituted at the 4- and 4'-positions. The results revealed that the complex of the present invention might be a promising dye for producing a high-performance photochemical cell.

Binuclear Ruthenium Complex Dye (B)

Reference Example B1

Synthesis of BiHexoStbpy

The complex, BiHexoStbpy was synthesized by reference to Journal of American Chemical Society, Vol. 128, pp. 4146-4154 (2006).

Example B1

Synthesis of the Binuclear Ruthenium Complex Dye (1b) {Ar=4-(Hexyloxy)Phenyl}

Example B1-A

Synthesis of the Mononuclear Ruthenium Complex (M-1); [Ru(Etcbpy)$_2$(H$_2$O)$_2$] (OTf)$_2$ The complex, [Ru(Etcbpy)$_2$(H$_2$O)$_2$](OTf)$_2$ was synthesized in the same way as in Example A2-A.

Example B1-B

Synthesis of the Mononuclear Ruthenium Complex (M-3); [(BiBzIm)Ru(BiHexoStbpy)$_2$] {Ar=4-(hexyloxy)phenyl}

Into a 200 mL three-necked flask were placed BiHexoStbpy (1.106 g, 1.973 mmol), [Ru(cod)Cl$_2$]$_n$ (0.268 g, 0.957 mmol) and N,N-dimethylformamide (100 mL). After deaeration, the mixture was refluxed for 34 minutes while being stirred under irradiation with 2.45 GHz microwave. The reaction solution was cooled down, and then the precipitate was collected by suction filtration, and washed with N,N-dimethylformamide, and then dried under vacuum, to provide [Ru(BiHexoStbpy)$_2$Cl$_2$] (0.779 g).

Subsequently, under argon atmosphere, into a 100 mL three-necked flask were placed Ru(BiHexoStbpy)$_2$Cl$_2$ (0.769 g, 0.595 mmol), BiBzImH$_2$ (0.153 g, 0.654 mmol) and ethylene glycol (25 mL). After deaeration, the mixture was refluxed for 21 minutes while being stirred under irradiation with 2.45 GHz microwave. The reaction solution was cooled down, and then acetone (70 mL) and water (30 mL) were added to the reaction solution. The resultant mixture was stirred at room temperature for 1 hour. After completion of stirring, the reaction solution was filtrated. And then, ammonium hexafluorophosphate (0.388 g, 2.380 mmol) dissolved in water (2 mL) was added to the resultant filtrate. The resultant mixture was stirred at room temperature for 30 minutes. The precipitate was washed with water, and then dried under vacuum, to provide [Ru(BiHexoStbpy)$_2$BiBzImH$_2$](PF$_6$)$_2$ (0.789 g).

Subsequently, into a 100 mL three-necked flask were placed [Ru(BiHexoStbpy)$_2$BiBzImH$_2$](PF$_6$)$_2$ (0.751 g, 0.430 mmol), methanol (11 mL) and a 10% lithium methoxide methanol solution (1.63 mL, 4.30 mmol). After deaeration, the mixture was refluxed for 1 hour. The reaction solution was cooled down, and then filtrated. The collected precipitate was washed with a 0.39 mol/L lithium methoxide methanol solution (which had the same concentration as the reaction solution), and then dried under vacuum, to provide the mononuclear ruthenium complex (M-3) [Ru(BiHexoStbpy)$_2$(BiBzIm)] (0.626 g).

Example B1-C

Synthesis of the Binuclear Ruthenium Complex Dye (1b) {Ar=4-(Hexyloxy)Phenyl}

Under argon atmosphere, into a 100 mL three-necked flask were placed the mononuclear ruthenium complex (M-1) (0.141 g, 0.139 mmol), the mononuclear ruthenium complex (M-3) (0.202 g, 0.139 mmol) and N,N-dimethylacetamide (25 mL). After deaeration, the mixture was refluxed for 22 minutes while being stirred under irradiation with 2.45 GHz microwave. The resultant reaction solution was cooled down, and then was concentrated under reduced pressure. And then, a 0.2 mol/L sodium hydroxide aqueous solution (36 mL) was added to the resultant concentrate, and the mixture was heated at 100° C. for 2 hours. The reaction solution was cooled down, and then the precipitate was collected by filtration, and washed with a mixture of acetone and diethyl ether (1:8).

Subsequently, the precipitate was suspended in water (50 mL), and then a 0.72 mol/L hexafluorophosphoric acid aqueous solution was added to the resultant mixture until pH became 3.5. After allowing the mixture to stand overnight, the precipitate was collected by filtration, and washed with a hexafluorophosphoric acid aqueous solution at pH 3.5, a mixture of acetone and diethyl ether (1:8) and diethyl ether, and then dried under vacuum, to provide the binuclear ruthenium complex dye (1b) (0.125 g).

The representative structure of the binuclear ruthenium complex dye is shown as the formula (1b). In the complex dye, one or more protons of carboxyl groups may dissociate.

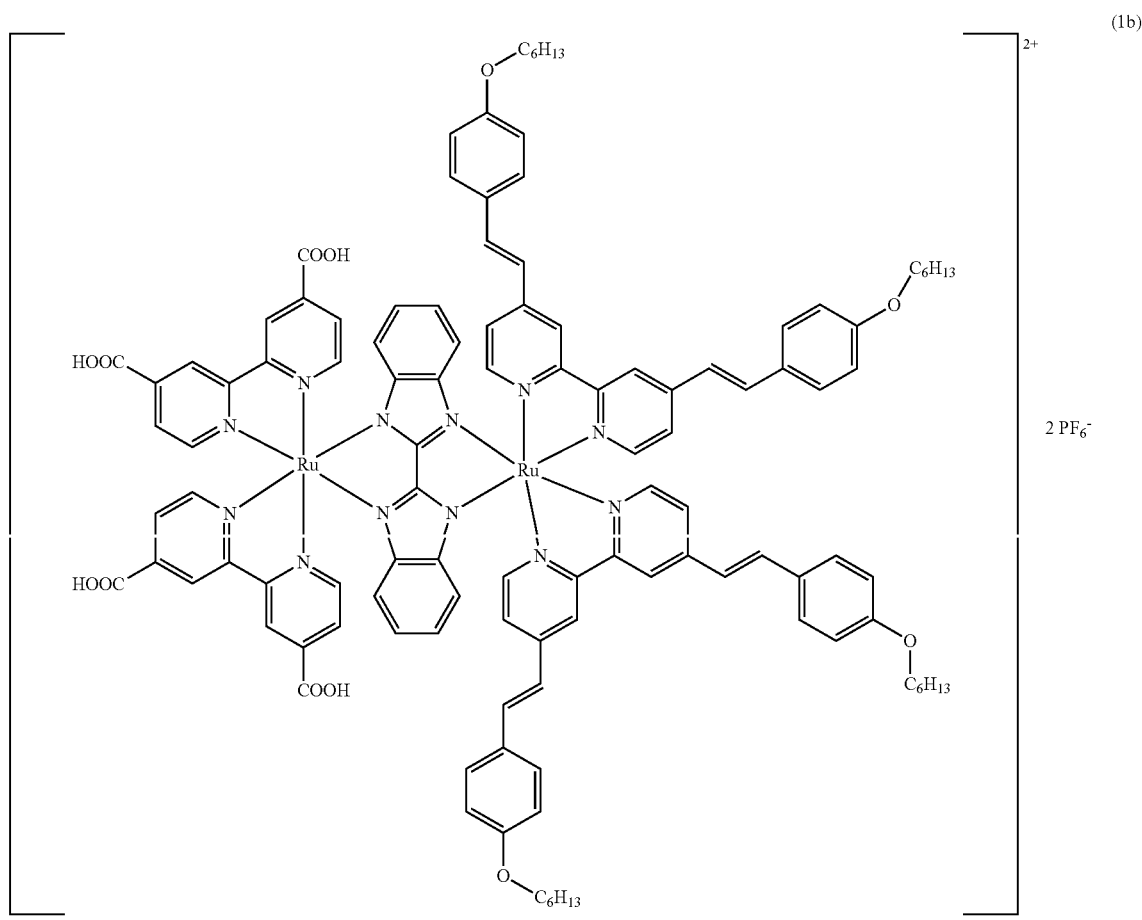

(1b)

Reference Example B2

Synthesis of the Binuclear Ruthenium Complex Dye (5) {the Complex Which is not Substituted with 4-(Hexyloxy)Styryl Groups as in Example B1}

The binuclear ruthenium complex dye (5) was synthesized according to a known method.

(5)

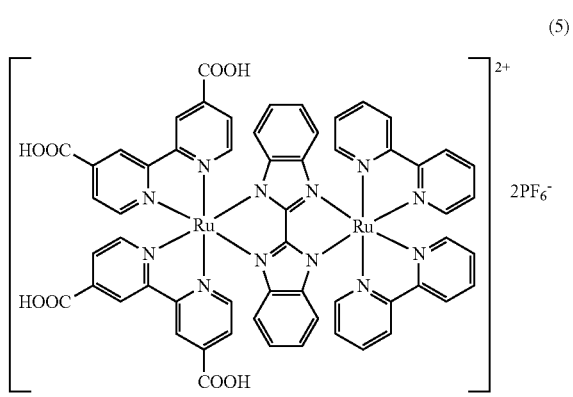

Example B2

Production of a Photochemical Cell

A dye-adsorbed porous titania electrode and a photochemical cell were prepared, using the complex dye, in the same way as in Examples A3-1 to A3-3.

Example B3

Measurement of Ultraviolet-Visible Absorption Spectrum

Two different types of $3 \times 10^{-5}$ mol/l solutions of the following complexes in ethanol were prepared, and ultraviolet-visible absorption spectra of the solutions were measured.

(1) Binuclear ruthenium complex of the present invention (1b; prepared in Example B1)
(2) Conventional binuclear ruthenium complex (5; prepared in Reference Example B2).

Figure 3:
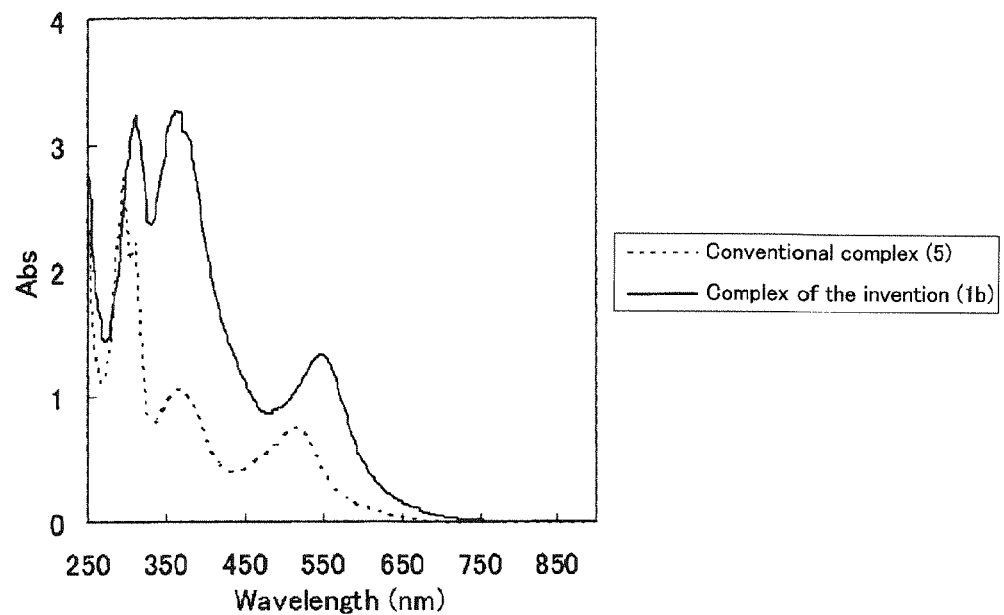
FIG. 3 is ultraviolet-visible absorption spectra of the binuclear ruthenium complex (1b) and the conventional binuclear ruthenium complex (5).

FIG. 3 shows ultraviolet-visible absorption spectra of the binuclear ruthenium complex (1b) and the conventional binuclear ruthenium complex (5).

The complex (binuclear ruthenium complex dye) of the present invention, i.e. the complex (1b) which is substituted with styryl groups at the 4- and 4'-positions on 2,2'-bipyridine ring, had a light absorption wavelength range shifted by about 40 nm to longer wavelength and had an absorbance of the longest wavelength peak 1.1 times higher under the same concentration conditions, as compared with the known binuclear ruthenium complex (5) which is unsubstituted at the 4- and 4'-positions. The results revealed that the complex of the present invention might be a promising dye for producing a high-performance photochemical cell.

Example B4

Synthesis of the Binuclear Ruthenium Complex Dye (2b) {Ar=4-(Hexyloxy)Phenyl, $R^1$=Hydrogen, Two $R^2$ are Joined Together to Form a Benzene Ring.}

Under argon atmosphere, into a 300 mL three-necked flask were placed dichloro-p-cymene ruthenium dimer (0.200 g, 0.326 mmol), BiHexoStbpy (0.366 g, 0.653 mmol) and N,N-dimethylformamide (100 mL). After deaeration, the mixture was reacted at 60° C. for 3.5 hours.

The reaction solution was cooled down, and then $H_2$dcbpy (0.160 g, 0.655 mmol) was added to the reaction solution. After re-deaeration, the mixture was reacted at 140° C. for 8.5 hours. The reaction solution was cooled down, and then a 1 mol/L sodium hydroxide aqueous solution (1.32 mL) and [Ru(phen)$_2$(BiBzIm)] (0.408 g, 0.588 mmol) were added to the reaction solution, and the mixture was refluxed and reacted for 3 hours.

The resultant reaction solution was concentrated under reduced pressure. And then, methanol (30 mL) and a 2 mol/L hydrochloric acid (0.1 mL) were added to the resultant concentrate, and the mixture was filtrated. The collected precipitate was dissolved in methanol, and then the resultant solution was subjected to liquid chromatography (developing solvent: methanol (containing 0.2 vol % of formic acid): water (containing 0.2 vol % of formic acid)=88:12 (volume ratio)) for fractionation, to collect the fraction containing a desired complex. The fraction was concentrated under reduced pressure, and then the resultant concentrate was suspended in methanol, acetone and a 0.4 mol/L hexafluorophosphoric acid aqueous solution (pH 2). After allowing the mixture to stand overnight, the solid material was collected by filtration, to provide the binuclear ruthenium complex dye (2b) (0.116 g).

The representative structure of the binuclear ruthenium complex dye is shown as the formula (2b). In the complex dye, one or more protons of carboxyl groups may dissociate.

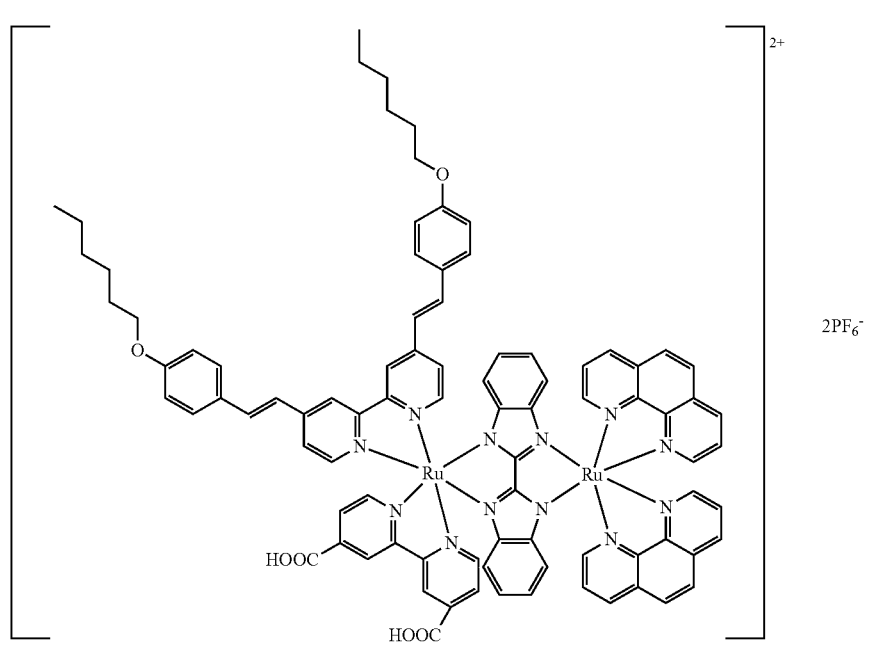

Reference Example B3

Synthesis of the Conventional Binuclear Ruthenium Complex Dye (6)

The binuclear ruthenium complex dye (6) was synthesized according to a known method.

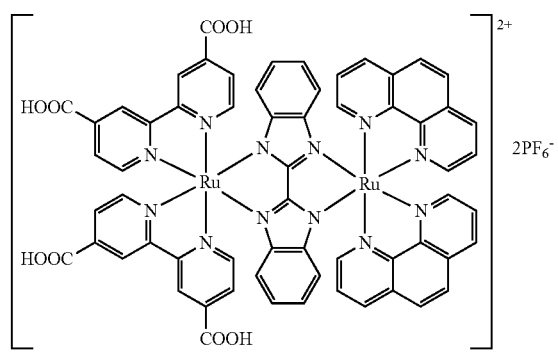

Example B5

Production of a Photochemical Cell

A dye-adsorbed porous titania electrode and a photochemical cell were prepared, using the complex dye, in the same way as in Examples A3-1 to A3-3.

Example B6

Measurement of Ultraviolet-Visible Absorption Spectrum

Two different types of $3\times10^{-5}$ mol/l solutions of the following complexes in ethanol were prepared, and ultraviolet-visible absorption spectra of the solutions were measured.
(1) Binuclear ruthenium complex of the present invention (2b; prepared in Example B4)
(2) Conventional binuclear ruthenium complex (6; prepared in Reference Example B3).

Figure 4:
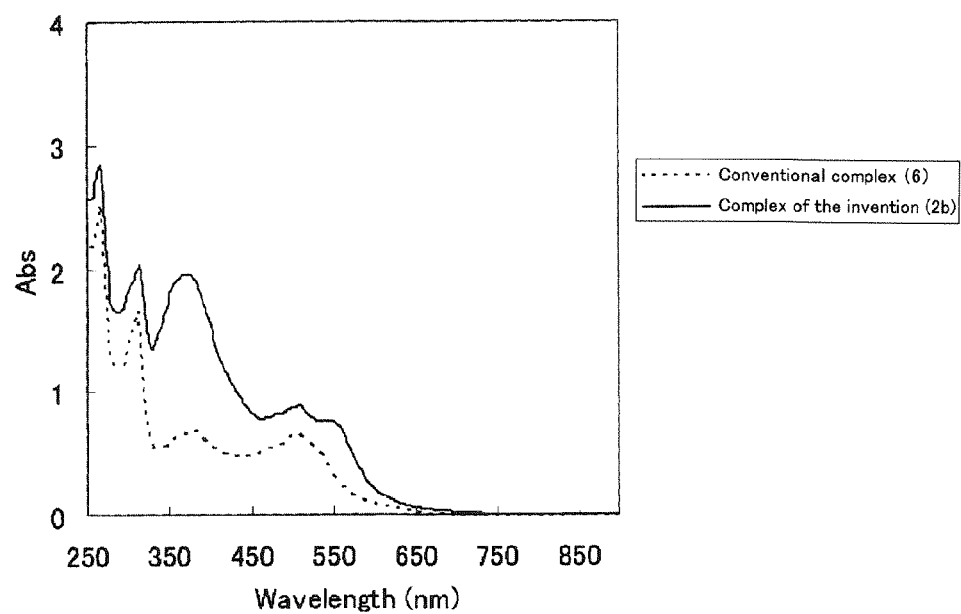
FIG. 4 is ultraviolet-visible absorption spectra of the binuclear ruthenium complex (2b) and the conventional binuclear ruthenium complex (6).

FIG. 4 shows ultraviolet-visible absorption spectra of the binuclear ruthenium complex (2b) and the conventional binuclear ruthenium complex (6).

Example B7

Measurement of Photoelectric Conversion Efficiency

The photoelectric conversion efficiencies of the photochemical cells thus obtained, which comprised the binuclear ruthenium complex of the present invention (2b) and the conventional binuclear ruthenium complex (6), respectively, were measured under irradiation with artificial solar light at 100 mW/cm², using a solar simulator made by EKO Instruments Co., Ltd. The results are shown in Table 1.

TABLE 1

| Complex dye | Conversion efficiency (%) |
|---|---|
| (2b) | 6.89 |
| (6) | 6.77 |

The complex (binuclear ruthenium complex dye) of the present invention, i.e. the complex (2b) which is substituted with styryl groups at the 4- and 4'-positions on 2,2'-bipyridine ring, had a light absorption wavelength range shifted by about 40 nm to longer wavelength and had an absorbance of the longest wavelength peak 1.1 times higher, as compared with the known binuclear ruthenium complex (6) which is substituted with dicarboxylic acid at the 4- and 4'-positions. In addition, the complex of the present invention exhibited relatively high photoelectric conversion efficiency. The results revealed that the complex of the present invention might be a promising dye for producing a high-performance photochemical cell.

Binuclear Ruthenium Complex Dye (C)

Example C1

Synthesis of the Binuclear Ruthenium Complex Dye (C2) {the Left Ru-Ligand: $R^1$=Nonyl Group, $R^2$=Hydrogen; the Right Ru-Ligand: Two $R^2$ are Joined Together to Form a Benzene Ring.}

Under argon atmosphere, into a 100 mL three-necked flask were placed dichloro-p-cymene ruthenium dimer (0.100 g, 0.164 mmol), dnbpy (0.139 g, 0.329 mmol) and N,N-dimethylformamide (50 mL). After deaeration, the mixture was reacted at 60° C. for 4 hours.

The reaction solution was cooled down, and then H$_2$dcbpy (0.080 g, 0.328 mmol) was added to the reaction solution. After re-deaeration, the mixture was reacted at 160° C. for 4 hours. The reaction solution was cooled down, and then a 1 mol/L sodium hydroxide aqueous solution (0.67 mL) and [Ru(phen)$_2$(BiBzIm)] (0.207 g, 0.298 mmol) were added to the reaction solution, and the mixture was refluxed and reacted for 5.5 hours.

The resultant reaction solution was concentrated under reduced pressure. The resultant concentrate was dissolved in methanol (30 mL), and then a hexafluorophosphoric acid aqueous solution at pH 2 (8 mL) was added to the solution, and the precipitate was separated by filtration.

Subsequently, a hexafluorophosphoric acid aqueous solution at pH 2 (16.5 mL) was added to the filtrate, and the precipitate was collected by filtration. The collected precipitate was dried, and then dissolved in methanol, and then the resultant solution was subjected to liquid chromatography (developing solvent: methanol (containing 0.2 vol % of formic acid)) for fractionation, to collect the fraction containing a desired complex. The fraction was concentrated under reduced pressure. The resultant concentrate was dissolved in methanol (10 mL), and then a hexafluorophosphoric acid aqueous solution at pH 2 (10 mL) was added to the solution. And then, the precipitate was collected by filtration, to provide the binuclear ruthenium complex dye (C2) (0.104 g).

The representative structure of the binuclear ruthenium complex dye is shown as the formula (C2). In the complex dye, one or more protons of carboxyl groups may dissociate.

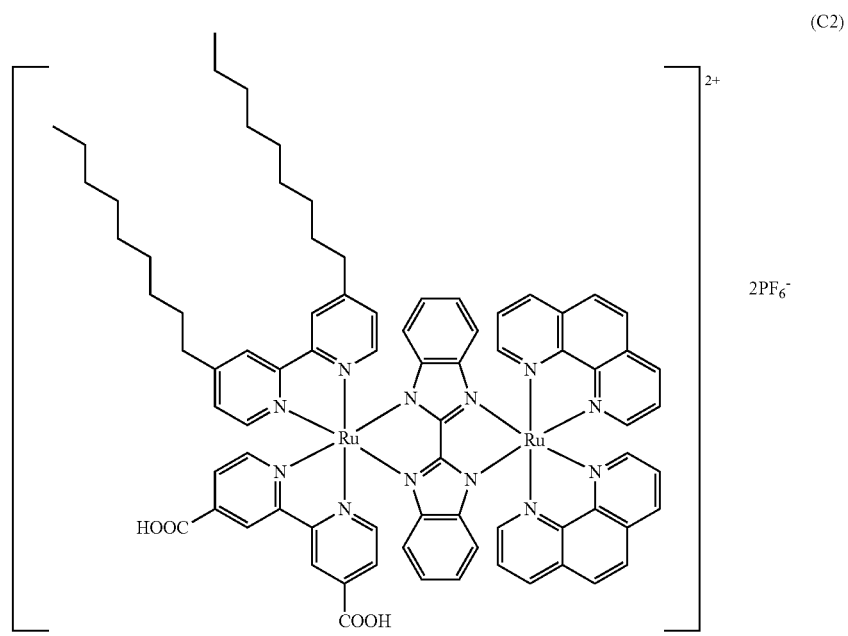

(C2)

Example C2

Synthesis of the Binuclear Ruthenium Complex Dye (C3) {$R^1$=Nonyl Group, $R^2$=Hydrogen}

Under argon atmosphere, into a 200 mL three-necked flask were placed dichloro-p-cymene ruthenium dimer (0.200 g, 0.327 mmol), dnbpy (0.277 g, 0.657 mmol) and N,N-dimethylformamide (100 mL). After deaeration, the mixture was reacted at 60° C. for 4 hours.

The reaction solution was cooled down, and then H$_2$dcbpy (0.160 g, 0.656 mmol) was added to the reaction solution. After re-deaeration, the mixture was reacted at 160° C. for 4 hours. The reaction solution was cooled down, and then a 1 mol/L sodium hydroxide aqueous solution (1.34 mL) and [Ru(dnbpy)$_2$(BiBzIm)] (0.678 g, 0.589 mmol) were added to the reaction solution, and the mixture was refluxed and reacted for 2 hours.

The resultant reaction solution was concentrated under reduced pressure. The resultant concentrate was dissolved in methanol, and then the resultant solution was subjected to liquid chromatography (developing solvent: methanol (containing 0.2 vol % of formic acid)) for fractionation, to collect the fraction containing a desired complex. The fraction was concentrated under reduced pressure. The resultant concentrate was dissolved in methanol (2.5 mL), and then a hexafluorophosphoric acid aqueous solution at pH 2 (2.5 mL) was added to the solution. And then, the precipitate was collected by filtration, to provide the binuclear ruthenium complex dye (C3) (0.096 g).

The representative structure of the binuclear ruthenium complex dye is shown as the formula (C3). In the complex dye, one or more protons of carboxyl groups may dissociate.

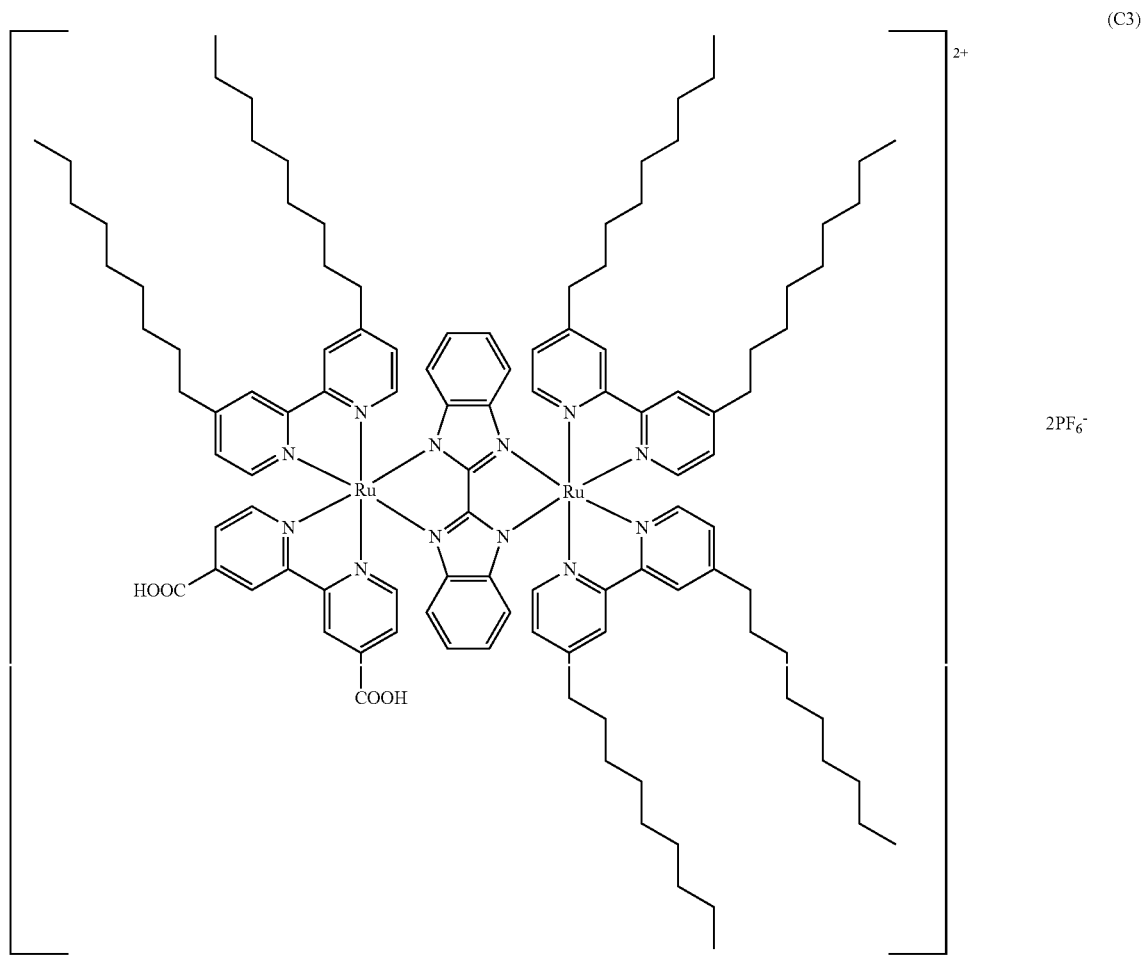

(C3)

Reference Example C1

Synthesis of the Binuclear Ruthenium Complex Dye (C4) {the Left Ru-Ligand: $R^1$=—COOH, $R^2$=Hydrogen; the Right Ru-Ligand: Two $R^2$ are Joined Together to Form a Benzene Ring.}

The binuclear ruthenium complex dye (C4) was synthesized according to a known method.

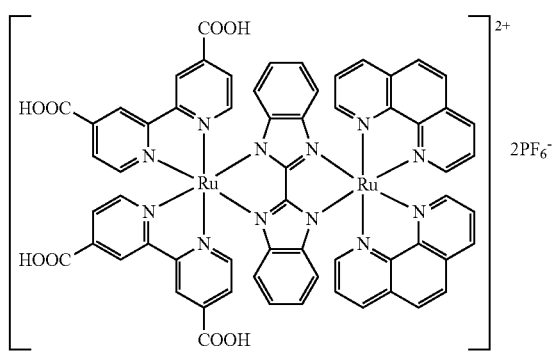

(C4)

Reference Example C2

Synthesis of the Binuclear Ruthenium Complex Dye (C5) {the Left Ru-Ligand: $R^1$=—COOH, $R^2$=Hydrogen; the Right Ru-Ligand: $R^1$=Nonyl Group, $R^2$=Hydrogen}

The binuclear ruthenium complex dye (C5) was synthesized according to a known method.

Example C3

Production of a Photochemical Cell

A dye-adsorbed porous titania electrode and a photochemical cell were prepared, using the complex dye, in the same way as in Examples A3-1 to A3-3.

Example C4

Evaluation of Durability

The photochemical cells thus obtained were left in the dark at 60° C. for the predetermined time period, and then returned to room temperature. Subsequently, the photoelectric conversion efficiencies ($\eta$) were measured under irradiation with artificial solar light at 100 mW/cm², using a solar simulator made by EKO Instruments Co., Ltd. Table 2 shows the retentions of the photoelectric conversion efficiencies after the photochemical cells were left in the dark at 60° C. for 5 days, based on the photoelectric conversion efficiency after the photochemical cells were left in the dark at 60° C. for 1 day as 100%.

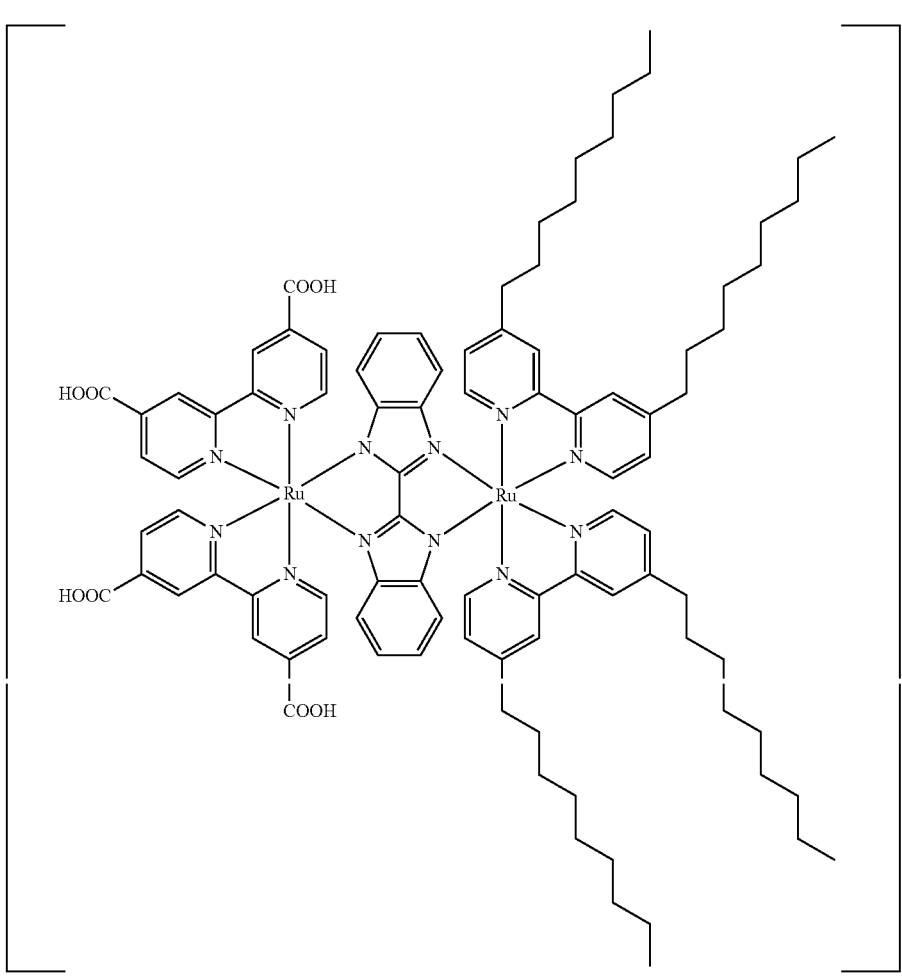

(C5)

TABLE 2

| Complex dye | Retention of Photoelectric conversion efficiency (%) | Notes |
|---|---|---|
| (C2) | 94 | Complex dye prepared in Example C1 |
| (C3) | 94 | Complex dye prepared in Example C2 |
| (C4) | 88 | Complex dye prepared in Reference Example C1 |
| (C5) | 85 | Complex dye prepared in Reference Example C2 |

The results revealed that the retention of the photoelectric conversion efficiency (i.e. durability) might be improved when using the complex dye of the present invention, as compared with the complex having a carboxyl group as $R^1$.

INDUSTRIAL APPLICABILITY

According to the present invention, there may be provided a metal complex dye having a higher absorption coefficient and capable of absorbing light of longer wavelength. There may be provided, by the use of the metal complex dye of the present invention, a photoelectric conversion element and a photochemical cell which may be capable of absorbing light over a wider wavelength range and convert solar light into electricity over a wide wavelength range, or be capable of absorbing a larger amount of solar light, and exhibit high photoelectric conversion efficiency.

According to the present invention, there may be provided a photoelectric conversion element and a photochemical cell which may have high durability.

The invention claimed is:

1. A binuclear ruthenium complex dye represented by the formula (1):

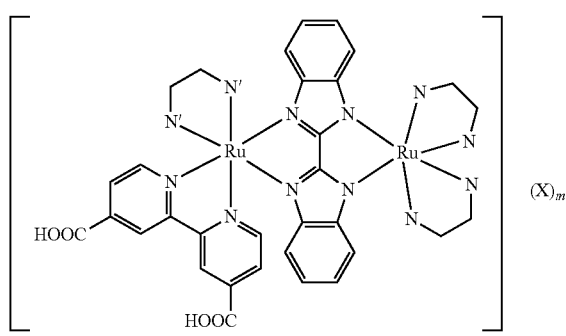

wherein
two

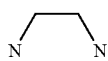

and

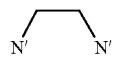

may be the same as, or different from each other, and each independently represents
a group represented by the formula (2-1):

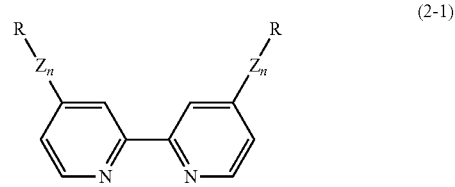

wherein
Z represents a 5-membered heteroarylene,
n represents a number of Z, which is an integer of from 0 to 4, and
R represents hydrogen, a linear or branched alkyl group having 1 to 18 carbon atoms, or carboxyl group,
with the proviso that two R may be the same as, or different from each other, and a plurality of Z may be the same as, or different from each other; or
a group represented by the formula (2-2):

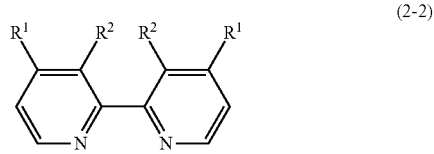

wherein
$R^1$ and $R^2$ each independently represents hydrogen, or a linear or branched alkyl group having 1 to 30 carbon atoms, or $R^1$ and $R^2$ present on the same pyridine ring or two $R^2$ may be joined together to form a ring,
with the proviso that two $R^1$ may be the same as, or different from each other, and two $R^2$ may be the same as, or different from each other; or
a group represented by the formula (2-3):

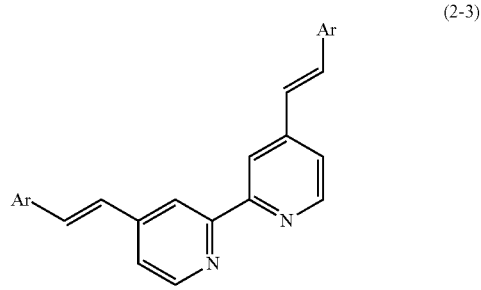

wherein
Ar represents an aryl group which may have a substituent, with the proviso that two Ar may be the same as, or different from each other; and X represents a counter ion; and
m represents a number of the counter ions needed to neutralize a charge of the complex;
with the proviso that
at least one of two

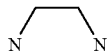

and

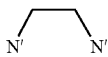

represents a group represented by the formula (2-1) in which n is an integer of from 1 to 4, or a group represented by the formula (2-3); or

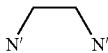

represents a group represented by the formula (2-2);
and proton(s) (H$^+$) of one or more carboxyl groups (—COOH) may dissociate.

2. A binuclear ruthenium complex dye according to claim 1, wherein at least one of two

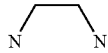

and

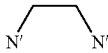

in the formula (1) represents a group represented by the formula (2-3).

3. A binuclear ruthenium complex dye according to claim 2, wherein two

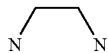

in the formula (1) represents a group represented by the formula (2-3), or a group represented by the formula (2-2); and

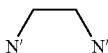

in the formula (1) represents a group represented by the formula (2-3).

4. A binuclear ruthenium complex dye according to claim 2, wherein Ar in the formula (2-3) represents phenyl group which may have a substituent.

5. A binuclear ruthenium complex dye according to claim 4, wherein Ar in the formula (2-3) represents a group represented by the formula (3-1):

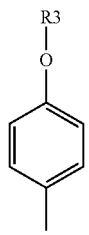

(3-1)

wherein
R3 represents a linear or branched alkyl group having 1 to 18 carbon atoms.

6. A photoelectric conversion element comprising a binuclear ruthenium complex dye according to claim 1; and a semiconductor particle.

7. A photoelectric conversion element according to claim 6, wherein the semiconductor particle is at least one selected from the group consisting of titanium oxide, zinc oxide and tin oxide.

8. A photochemical cell comprising a photoelectric conversion element according to claim 6.

9. A photochemical cell comprising a photoelectric conversion element according to claim 6 as an electrode, a counter electrode, and an electrolyte layer between them.

10. A process for producing a photoelectric conversion element, comprising a step of:
immersing a semiconductor particle in a solution containing a binuclear ruthenium complex dye according to claim 1.

11. A process for producing a photoelectric conversion element, comprising steps of:
forming a semiconductor layer comprising a semiconductor particle on a conductive support; and
immersing the semiconductor layer in a solution containing a binuclear ruthenium complex dye according to claim 1.

12. A binuclear ruthenium complex dye according to claim 1, wherein at least one of two

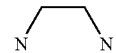

and

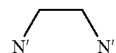

in the formula (1) represents a group represented by the formula (2-1) in which n is an integer of from 1 to 4, and R represents hydrogen, or a linear or branched alkyl group having 1 to 18 carbon atoms.

13. A binuclear ruthenium complex dye according to claim 12, wherein two

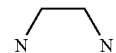

the formula (1) represents a group represented by the formula (2-1) in which n is an integer of from 1 to 4, and R represents hydrogen, or a linear or branched alkyl group having 1 to 18 carbon atoms, or a group represented by the formula (2-2); and

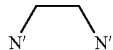

in the formula (1) represents a group represented by the formula (2-1) in which n is an integer of from 1 to 4, and R represents hydrogen, or a linear or branched alkyl group having 1 to 18 carbon atoms.

14. A binuclear ruthenium complex dye according to claim 13, wherein tow

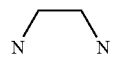

in the formula (1) represents a group represented by the formula (2-2) in which $R^1$ represents a linear or branched alkyl group having 1 to 30 carbon atoms, and $R^2$ represents hydrogen; and

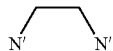

in the formula (1) represents a group represented by the formula (2-1) in which n is an integer of from 1 to 4, and R represents hydrogen, or a linear or branched alkyl group having 1 to 18 carbon atoms.

15. A binuclear ruthenium complex dye according to claim 12, wherein

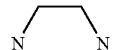

in the formula (1) represents a group represented by the formula (2-1) in which n is an integer of from 1 to 4, and R represents hydrogen, or a linear or branched alkyl group having 1 to 18 carbon atoms; and

in the formula (1) represents a group represented by the formula (2-1) in which n is 0, and R represents carboxyl group.

16. A binuclear ruthenium complex dye according to claim 3, wherein two

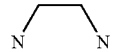

in the formula (1) represents a group represented by the formula (2-2); and

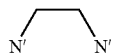

in the formula (1) represents a group represented by the formula (2-3).

17. A binuclear ruthenium complex dye according to claim 16, wherein two

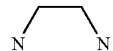

in the formula (1) represents a group represented by the formula (2-2) in which $R^1$ represents hydrogen, and two $R^2$ are joined together to form a benzene ring; and

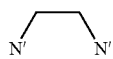

in the formula (1) represents a group represented by the formula (2-3).

18. A binuclear ruthenium complex dye according to claim 2, wherein two

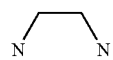

in the formula (1) represents a group represented by the formula (2-3); and

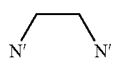

in the formula (1) represents a group represented by the formula (2-1) in which n is 0, and R represents carboxyl group.

19. A binuclear ruthenium complex dye according to claim 1, wherein two

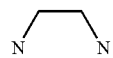

in the formula (1) represents a group represented by the formula (2-2); and

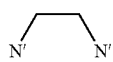

in the formula (1) represents a group represented by the formula (2-2) in which $R^1$ and/or $R^2$ represents a linear or branched alkyl group having 1 to 30 carbon atoms.

20. A binuclear ruthenium complex dye according to claim 19, wherein two

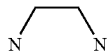

in formula (1) represents a group represented by the formula (2-2); and

in the formula (1) represents a group represented by the formula (2-2) in which $R^1$ represents a linear or branched alkyl group having 1 to 30 carbon atoms, and $R^2$ represents hydrogen.

21. A binuclear ruthenium complex dye according to claim 20, wherein two

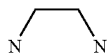

in the formula (1) represents a group represented by the formula (2-2) in which $R^1$ represents hydrogen, and two $R^2$ are joined together to form a benzene ring; and

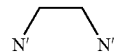

in the formula (1) represents a group represented by the formula (2-2) in which $R^1$ represents a linear or branched alkyl group having 1 to 30 carbon atoms, and $R^2$ represents hydrogen.

22. A binuclear ruthenium complex dye according to claim 20, wherein two

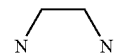

in the formula (1) represents a group represented by the formula (2-2) in which $R^1$ represents a linear or branched alkyl group having 1 to 30 carbon atoms, and $R^2$ represents hydrogen; and

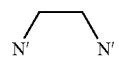

in the formula (1) represents a group represented by the formula (2-2) in which $R^1$ represents a linear or branched alkyl group having 1 to 30 carbon atoms, and $R^2$ represents hydrogen.

\* \* \* \* \*